US012721838B2

(12) United States Patent
Ghosh et al.

(10) Patent No.: US 12,721,838 B2
(45) Date of Patent: Sep. 1, 2026

(54) DACLATASVIR FOR USE IN TREATING LUNG AND PROSTATE CANCER

(71) Applicant: Henry Ford Health System, Detroit, MI (US)

(72) Inventors: Jagadananda Ghosh, Troy, MI (US); Jitender Monga, Farmington Hills, MI (US)

(73) Assignee: Henry Ford Health System, Detroit, MI (US)

( * ) Notice: Subject to any disclaimer, the term of this patent is extended or adjusted under 35 U.S.C. 154(b) by 695 days.

(21) Appl. No.: 18/000,756

(22) PCT Filed: Jun. 4, 2021

(86) PCT No.: PCT/US2021/036038
§ 371 (c)(1),
(2) Date: Dec. 5, 2022

(87) PCT Pub. No.: WO2021/248093
PCT Pub. Date: Dec. 9, 2021

(65) Prior Publication Data

US 2024/0050415 A1 Feb. 15, 2024

Related U.S. Application Data

(60) Provisional application No. 63/035,353, filed on Jun. 5, 2020.

(51) Int. Cl.
*A61K 31/4178* (2006.01)
*A61K 31/4166* (2006.01)
*A61P 35/00* (2006.01)

(52) U.S. Cl.
CPC ...... *A61K 31/4178* (2013.01); *A61K 31/4166* (2013.01); *A61P 35/00* (2018.01)

(58) Field of Classification Search
CPC .. A61K 31/4178; A61K 31/4166; A61P 35/00
See application file for complete search history.

(56) References Cited

FOREIGN PATENT DOCUMENTS

| | | |
|---|---|---|
| WO | WO2007084757 A2 | 7/2007 |
| WO | WO2008021927 A2 | 2/2008 |
| WO | WO2008021928 A2 | 2/2008 |
| WO | WO2009020825 A1 | 2/2009 |
| WO | WO2009020828 A1 | 2/2009 |
| WO | WO2011059850 A1 | 5/2011 |

OTHER PUBLICATIONS

Gandhi et al. Daclatasvir: a Review of Preclinical and Clinical Pharmacokinetics (Clin Pharmacokinet, 57:911-928). (Year: 2018).*
Zhang et al. The role of tribbles homolog 2 in cell proliferation. Cell Commun Signal 23, 5 (2025). (Year: 2025).*
Anonymous, "Enzalutamide—Drug Summary," Prescribers' Digital Reference, pp. 1-21, Sep. 29, 2021.
El-Shabrawi, Mortada HF, et al., "Effects of Dual Sofosbuvir/Daclatasvir Therapy on, Chronic Hepatitis C Infected, Survivors of Childhood Malignancy," World Journal of Clinical Cases, vol. 7, No. 16, pp. 2247-2255, Aug. 26, 2019.
Grandinetti, K.B. et al., " Overexpression of TRIB2 in Human Lung Cancers Contributes to Tumorigensis Through Downregulation of V/EBP [alpha]", Oncogene, vol. 30, No. 3, pp. 3328-3335, Mar. 13, 2011.
Hill, Richard et al., TRIB2 Confers Resistance to Anti-Cancer Therapy by Activating the Serine/Threonine Protein Kinase AKT, Nature Communications, vol. 8, No. 1, pp. 1-9, Apr. 1, 2017.
Written Opinion of the International Searching Authority issued on Oct. 10, 2021 for International Application No. PCT/US2021/036038.
International Search Report issued on Oct. 10, 2021 for International Application No. PCT/US2021/036038.
Monga, Jitender et al., "Abstract 1325: Overexpression of Tribbles 2 Enhances Prostrate Cancer Cell Growth and Contributes to Enzalutamide Resistance," Proceedings: AACR Annual Meeting, pp. 1-4, Apr. 10, 2021.
Sultanik, Philippe et al., "Regression of an HCV-Associated Disseminated Marginal Zone Lymphoma Under IFN-Free Antiviral Treatment," Blood, vol. 125, No. 15, pp. 2446-2447, Apr. 9, 2015.
Wang, Ping-Yu et al., "Let-7c Inhibits A549 Cell Proliferation Through Oncogenic TRIB2 Related Factors," FEBS Letters, vol. 587, No. 16, pp. 2675-2681, Jul. 11, 2013.
Examination Report issued by the European Patent Office for application 21736129.4 Oct. 9, 2024.
Examination Report issued by the European Patent Office for application 21736129.4, Feb. 14, 2024.
Communication pursuant to Rule 161(1) and 162 issued by the European Patent Office for aplication 21736129.4, Jan. 13, 2023.
International Preliminary Report on Patentability issued for PCT/US2021/036038 on Dec. 15, 2022.

* cited by examiner

*Primary Examiner* — Adam C Milligan
*Assistant Examiner* — William Y Lee
(74) *Attorney, Agent, or Firm* — Reising Ethington P.C.

(57) ABSTRACT

The present invention discloses daclatasvir (DCV) for use in the treatment and/or prevention of cancer, preferably lung cancer and/or prostate cancer, more preferably enzalutamide-resistant prostate cancer.

2 Claims, 18 Drawing Sheets

Specification includes a Sequence Listing.

| Compound | Luciferase activity (%) | Compound | Luciferase activity (%) |
|---|---|---|---|
| Dichlorphrnamide | 100 | Darunavir | 93 |
| Ranolazine | 100 | Niraparib tosylate | 93 |
| 6-Acetamidohexanoic | 100 | Clofibric acid | 87 |
| Alcaftadine | 100 | Ajamaline | 93 |
| Temsirolmus | 94 | Sulfamethizole | 94 |
| Oxaceprol | 100 | Fimasartan | 88 |
| Mianserin | 55 | Anagrelide | 92 |
| Dolutegravir | 100 | Nadifloxacin | 96 |
| Nilotinib | 99 | Ponatinib | 42 |
| Efonidipine | 98 | Valnemulin | 83 |
| Dirithromycin | 100 | Mozavaptan | 86 |
| Clebopride | 100 | Dipyridamole | 98 |
| Ibudilast | 85 | Lansoprazole | 78 |
| Ramelteon | 100 | Atropine | 67 |
| Chlormerazanoine | 100 | Olmesartan | 80 |
| Famotidine | 100 | Estrone | 82 |
| Busulfan | 100 | Hydroxyfasudil | 46 |
| Epalrestat | 53 | Sulfaguanidine | 84 |
| Ornipressin | 27 | Prazosin | 49 |
| Ampiroxicam | 28 | Tigecycline | 63 |
| Droperidol | 100 | Doxorubicin | 28 |
| Nilvadipine | 89 | Ledipasvir | 100 |
| Triamterene | 100 | Levocarnitine | 84 |
| Methacholine | 99 | Sulfadiazine | 70 |
| Doxycycline | 91 | Guanfacine | 100 |
| Alprenolol | 91 | Tavaborole | 75 |
| Niclosamide | 62 | Isosorbide | 91 |
| Irinotecan | 85 | Betamipron | 87 |
| Fenofibrate | 92 | Udenafil | 100 |
| Ethambutol | 98 | Milnacipran | 85 |
| Gadodiamide | 89 | Carbidopa | 92 |
| Teniposide | 70 | Imipramine | 86 |
| Vincamine | 80 | Telotristat etiprate | 94 |
| Pemirolast | 88 | Trimetazidine | 100 |
| Cromolyn | 93 | Ronidazole | 100 |
| 5-Aminosalicyclic acid | 84 | Malathion | 91 |
| Tamibarotene | 100 | Danofloxacin | 81 |
| Dapoxetine | 88 | Azasetron | 100 |
| Telbivudine | 91 | Plerixafor | 93 |
| Mexiletine | 86 | Meloxicam | 100 |
| Noscapine | 100 | Tegafur | 100 |
| Efavirenz | 89 | Terconazole | 82 |
| Penciclovir | 97 | Dabrafenib | 72 |
| Tebipenem pivoxil | 100 | Triamcinolone | 72 |
| Venetoclax | 184 | Vorapaxar | 59 |
| Chlorambucil | 96 | Proparacaine | 88 |
| Resperine | 91 | Erlotinib | 50 |
| Clarithromycin | 97 | Daclatasvir | 28 |
| Etomidate | 100 | Pyridostigmine | 76 |
| Dexrazoxane | 100 | Fingolimod | 80 |
| Paroxetine | 93 | Minaprine | 79 |
| Penfluridol | 71 | Ticarcillin | 87 |
| Fluocinonide | 78 | Budesonide | 83 |

FIG. 1A

```
        10         20         30         40         50
MNIHRSTPIT IARYGRSRNK TQDFEELSSI RSAEPSQSFS PNLGSPSPPE
        60         70         80         90        100
TPNLSHCVSC IGKYLLLEPL EGDHVFRAVH LHSGEELVCK VFDISCYQES
       110        120        130        140        150
LAPCFCLSAH SNINQITEII LGETKAYVFF ERSYGDMHSF VRTCKKLREE
       160        170        180        190        200
EAARLFYQIA SAVAHCHDGG LVLRDLKLRK FIFKDEERTR VKLESLEDAY
       210        220        230        240        250
ILRGDDDSLS DKHGCPAYVS PEILNTSGSY SGKAADVWSL GVMLYTMLVG
       260        270        280        290        300
RYPFHDIEPS SLFSKIRRGQ FNIPETLSPK AKCLIRSILR REPSERLTSQ
       310        320        330        340
EILDHPWFST DFSVSNSAYG AKEVSDQLVP DVNMEENLDP FFN
```

FIG. 13

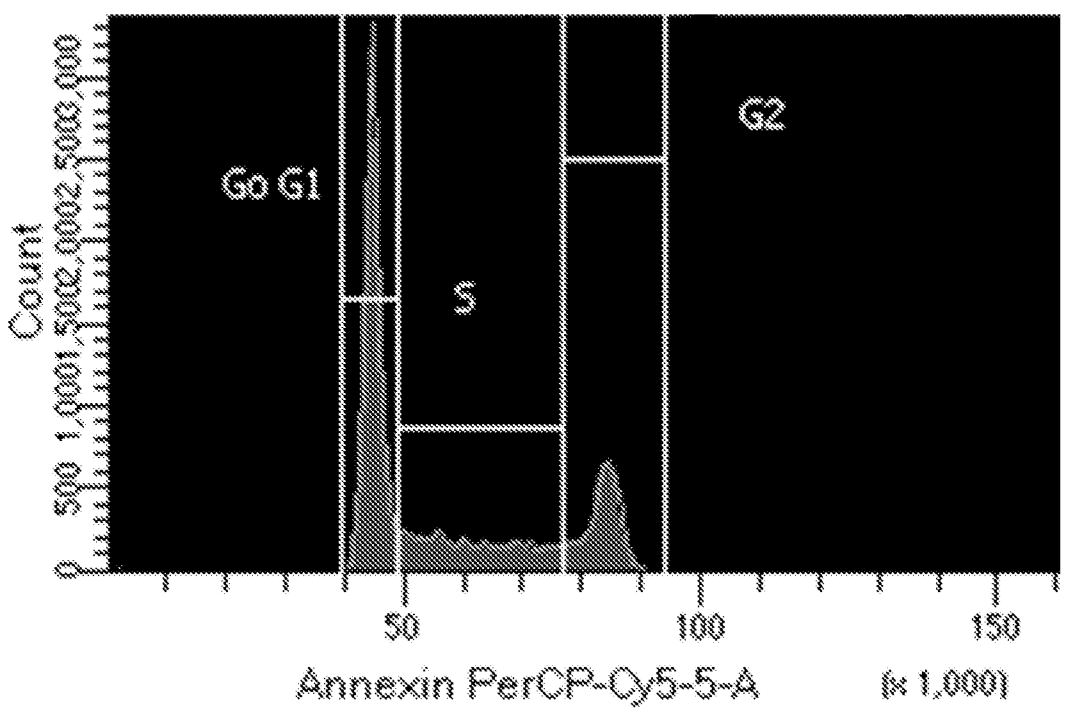

FIG. 14

DACLATASVIR FOR USE IN TREATING LUNG AND PROSTATE CANCER

CROSS REFERENCE TO RELATED APPLICATIONS

This application is a 35 U.S.C. § 371 National Stage filing of International Application No. PCT/US2021/036038, filed Jun. 4, 2021, which claims the benefit of, and priority to U.S. Provisional Application No. 63/035,353, filed on Jun. 5, 2020. The entire contents of the aforementioned applications are incorporated herein by reference in their entireties.

SEQUENCE

This application incorporates by reference in its entirety the Sequence Listing entitled "seq_ST25.txt" (4 KB), which was created on Nov. 2, 2023 at 3:09 PM.

TECHNICAL FIELD

New methods of preventing and/or treating cancer, are described and claimed, including, inter alia, the use of therapeutically effective amount of daclatasvir (DCV); and the use of the same in a subject in need thereof having a cancer that expresses higher levels of Tribbles homolog 2 (TRIB2), relative to non-cancer cells, are likewise described and claimed.

BACKGROUND

Enzalutamide is an androgen receptor inhibitor used for the treatment of prostate cancer. Although patients show initial response to treatment, resistance to enzalutamide can develop. Enzalutamide-resistant prostate cancer (ERPC) is an incurable, end-stage disease for which no suitable targets or agents are currently available. Hence, there is a need for the identification of new therapeutic approaches that can be implemented in the treatment of cancer.

Lung cancer is the leading cause of cancer-related mortality worldwide. Recent developments in targeted therapies have led to a treatment paradigm shift in non-small-cell lung cancer (NSCLC). Mok T S, Wu Y L, Thongprasert S, Yang C H, Chu D T, Saijo N, Sunpaweravong P, Han B, Margono B, Ichinose Y, Nishiwaki Y, Ohe Y, Yang J J, Chewaskulyong B, Jiang H, Duffield E L, Watkins C L, Armour A A, Fukuoka M. Gefitinib or carboplatin-paclitaxel in pulmonary adenocarcinoma. N Engl J Med. 2009 Sep. 3; 361(10): 947-57. Maemondo M, Inoue A, Kobayashi K, Sugawara S, Oizumi S, Isobe H, Gemma A, Harada M, Yoshizawa H, Kinoshita I, Fujita Y, Okinaga S, Hirano H, Yoshimori K, Harada T, Ogura T, Ando M, Miyazawa H, Tanaka T, Saijo Y, Hagiwara K, Morita S, Nukiwa T; North-East Japan Study Group. Gefitinib or chemotherapy for non-small-cell lung cancer with mutated EGFR. N Engl J Med. 2010 Jun. 24; 362(25):2380-8. Epidermal growth factor receptor (EGFR) tyrosine kinase inhibitors (TKIs), gefitinib and erlotinib, and the anaplastic lymphoma kinase (ALK) TKI, crizotinib, have shown clinical activity in NSCLC patients with EGFR mutations or ALK gene rearrangements. Kwak E L, Bang Y J, Camidge D R, Shaw A T, Solomon B, Maki R G, Ou S H, Dezube B J, Jänne P A, Costa D B, Varella-Garcia M, Kim W H, Lynch T J, Fidias P, Stubbs H, Engelman J A, Sequist L V, Tan W, Gandhi L, Mino-Kenudson M, Wei G C, Shreeve S M, Ratain M J, Settleman J, Christensen J G, Haber D A, Wilner K, Salgia R, Shapiro G I, Clark J W, Iafrate A J. Thus, it is becoming more important to identify key driver genes in lung cancer and Enzalutamide-resistant prostate cancer and to develop therapies for each subset of patients.

SUMMARY

As described herein, Tribbles homolog 2 (TRIB2) plays a role in the survival of enzalutamide-resistant prostate cancer (ERPC) cells. Currently, there are no inhibitors of TRIB2. The present disclosure demonstrates that the antiviral drug daclatasvir (DCV) can inhibit TRIB2 protein and that DCV displays anti-tumor effects in TRIB2-positive cancer cells, including ERPC cells and TRIB2-positive lung cancer, including but not limited to: non-small cell lung cancer, small cell lung cancer, oat cell cancer, adenocarcinoma, squamous cell carcinoma, large cell (undifferentiated) carcinoma, papillary carcinoma, adenosquamous carcinoma, carcinoid tumors, adenoid cystic carcinomas lymphomas, and sarcomas, and sarcomatoid carcinoma. In various embodiments, the lung cancers described in the foregoing are TRIB2-positive lung cancers. The present disclosure provides an effective method for treating TRIB2-positive cancer, such as prostate cancer, in particular, ERPC, and/or lung cancer by administering a therapeutically effective amount of daclatasvir (DCV) to a subject in need thereof.

The present disclosure describes a method of preventing or treating cancer in a subject in need thereof, said method comprising administering a therapeutically effective amount of daclatasvir (DCV) to a subject suffering from cancer. In various embodiments, the cancer is TRIB2-positive cancer.

In addition, the present disclosure describes a method of treating cancer in a subject in need thereof, said method comprising administering to the subject a therapeutically effective amount of daclatasvir (DCV), wherein cancer cells in the subject express higher levels of Tribbles homolog 2 (TRIB2) compared to levels of TRIB2 expressed by counterpart non-cancer cells of the same cellular type of cells adjacent to the cancer cells that are non-cancerous and/or non-hyper-proliferative.

In addition, the present disclosure describes a method of preventing or treating cancer in a subject in need thereof, said method comprising administering a therapeutically effective amount of daclatasvir (DCV) to a subject suffering from cancer.

In addition, the present disclosure describes a method of preventing or treating cancer in a subject in need thereof, said method comprising administering a therapeutically effective amount of daclatasvir (DCV) to a subject suffering from cancer, wherein the cancer is prostate cancer, or lung cancer.

In addition, the present disclosure describes a method of preventing or treating cancer in a subject in need thereof, said method comprising administering a therapeutically effective amount of daclatasvir (DCV) to a subject suffering from cancer, wherein, the subject is treatment naïve, or has previously been treated with an anti-cancer agent and is refractory to the anti-cancer agent.

In addition, the present disclosure describes a method of preventing or treating cancer in a subject in need thereof, said method comprising administering a therapeutically effective amount of daclatasvir (DCV) to a subject suffering from cancer, wherein the prior anti-cancer agent is androgen deprivation therapy (ADT).

In addition, the present disclosure describes a method of preventing or treating cancer in a subject in need thereof, said method comprising administering a therapeutically effective amount of daclatasvir (DCV) to a subject suffering from cancer, wherein the prostate cancer is resistant to ADT; wherein, optionally, the subject has previously been treated with ADT and the cancer has developed resistance to ADT.

In addition, the present disclosure describes a method of preventing or treating cancer in a subject in need thereof, said method comprising administering a therapeutically effective amount of daclatasvir (DCV) to a subject suffering from cancer, wherein the ADT is pharmaceutical ADT; wherein, optionally, the pharmaceutical ADT is treatment with an antiandrogen.

In addition, the present disclosure describes a method of preventing or treating cancer in a subject in need thereof, said method comprising administering a therapeutically effective amount of daclatasvir (DCV) to a subject suffering from cancer, wherein the antiandrogen is enzalutamide.

In addition, the present disclosure describes a method of preventing or treating cancer in a subject in need thereof, said method comprising administering a therapeutically effective amount of daclatasvir (DCV) to a subject suffering from cancer, wherein the cancer is enzalutamide-resistant prostate cancer (ERPC).

In addition, the present disclosure describes a method of preventing or treating cancer in a subject in need thereof, said method comprising administering a therapeutically effective amount of daclatasvir (DCV) to a subject suffering from cancer, wherein the cancer is lung cancer.

In addition, the present disclosure describes a method of preventing or treating cancer in a subject in need thereof, said method comprising administering a therapeutically effective amount of daclatasvir (DCV) to a subject suffering from cancer, wherein a cancer cell from the subject's cancer expresses higher levels of Tribbles homolog 2 (TRIB2) compared to levels of TRIB2 in a counterpart non-cancer cell.

In addition, the present disclosure describes a method of preventing or treating cancer in a subject in need thereof, said method comprising administering a therapeutically effective amount of daclatasvir (DCV) to a subject suffering from cancer, wherein: (i) the cancer cell expresses higher levels of TRIB2 compared to levels of TRIB2 in the counterpart non-cancer cell of the subject; and/or (ii) the cancer cell expresses higher levels of TRIB2 compared to levels of TRIB2 in the counterpart non-cancer cell derived from a subject not suffering from cancer.

In addition, the present disclosure describes a method of preventing or treating cancer in a subject in need thereof, said method comprising administering a therapeutically effective amount of daclatasvir (DCV) to a subject suffering from cancer, wherein the cancer cell and the non-cancer cell are derived from the same type of tissue; wherein, optionally, the cancer cell and the non-cancer cell are derived from prostate tissue.

In addition, the present disclosure describes a method of preventing or treating cancer in a subject in need thereof, said method comprising administering a therapeutically effective amount of daclatasvir (DCV) to a subject suffering from cancer, wherein the DCV is administered as part of a combination therapy; wherein, optionally, the combination therapy comprises DCV and enzalutamide.

In addition, the present disclosure describes a method of preventing or treating cancer in a subject in need thereof, said method comprising administering a therapeutically effective amount of daclatasvir (DCV) to a subject suffering from cancer, wherein the treating comprises: (i) reducing a tumor volume or burden in the subject; (ii) inhibiting tumor growth in a subject; and/or (iii) reducing the levels of TRIB2 protein in a tumor of the subject.

The present disclosure describes a method of treating cancer in a subject in need thereof, said method comprising administering to the subject a therapeutically effective amount of daclatasvir (DCV), wherein cancer cells in the subject express higher levels of Tribbles homolog 2 (TRIB2) compared to levels of TRIB2 expressed by counterpart non-cancer cells.

In addition, the present disclosure describes a method of treating cancer in a subject in need thereof, said method comprising administering to the subject a therapeutically effective amount of daclatasvir (DCV), wherein cancer cells in the subject express higher levels of Tribbles homolog 2 (TRIB2) compared to levels of TRIB2 expressed by counterpart non-cancer cells, wherein: (i) the counterpart non-cancer cells are derived from the subject; and/or (ii) the counterpart non-cancer cells are derived from a subject not suffering from cancer.

In addition, the present disclosure describes a method of treating cancer in a subject in need thereof, said method comprising administering to the subject a therapeutically effective amount of daclatasvir (DCV), wherein cancer cells in the subject express higher levels of Tribbles homolog 2 (TRIB2) compared to levels of TRIB2 expressed by counterpart non-cancer cells, wherein the cancer cells and the counterpart non-cancer cells are derived from prostate tissue; wherein, optionally, the cancer cells and the counterpart non-cancer cells are cells of prostate glands.

In addition, the present disclosure describes a method of treating cancer in a subject in need thereof, said method comprising administering to the subject a therapeutically effective amount of daclatasvir (DCV), wherein cancer cells in the subject express higher levels of Tribbles homolog 2 (TRIB2) compared to levels of TRIB2 expressed by counterpart non-cancer cells, wherein the cancer cells and the counterpart non-cancer cells are derived from lung tissue; wherein, the cancer cells are, or derived from non-small cell lung cancer (NSCLC), small cell lung cancer, papillary carcinoma, adenocarcinomas, squamous cell carcinomas, bronchioalveolar carcinomas, and large cell carcinomas.

BRIEF DESCRIPTION OF THE DRAWINGS

FIG. 1A-FIG. 1C show representative compounds from a high-throughput screen to identify compounds that down-regulate Tribbles homolog 2 (TRIB2). FIG. 1A is a table illustrating the effects of a representative set of 104 FDA-approved compounds on Trib2-Luciferase fusion construct-transfected Human foreskin fibroblast (HFF) cells. Here, daclatasvir (DCV) is highlighted in red. The column on the far right depicts the percent luciferase activity remaining subsequent to a given drug treatment, normalized to a control solvent (0.4% DMSO) treatment taken as 100%. FIG. 1B depicts the chemical structure of daclatasvir (DCV). FIG. 1C depicts the chemical structure of ledipasvir (LDV).

FIG. 2A-FIG. 2B show the effects of DCV versus other compounds on TRIB2-positive cancer cells. FIG. 2A shows a western blot of lysates from LNCaP-ENR cells treated with 10 μM of various drugs for 24 hours. The labeled lanes are as follows: (1) Control, i.e., solvent (0.4% DMSO) treatment (DMSO was chosen as the control because the compounds tested are solubilized in DMSO, the final concentration of DMSO added to the cells along with drug is ~0.4%); (2) Ampiroxicam; (3) Prazosin; (4) Daclatasvir; (5) Ornipressin; (6) Ledipasvir; (7) Lapatinib; (8) Vorapaxar; (9) Ponatinib; (10) Mianserin. FIG. 2B shows cell viability of LNCaP-ENR cells treated with the indicated doses of DCV or LDV for 72 hours. Results are normalized to control-treated cells (i.e., control DMSO (0.4%)-treated cells). Data is representative of 3 replicates. Error bars represent standard deviation from the mean.

FIG. 3A shows a western blot of lysates from LNCaP-ENR cells treated with the indicated concentrations of DCV or control (0.4% DMSO) treatment for 24 hours. FIG. 3B shows treatment of ERPC cells with the indicated concentrations of DCV in soft-agar colony formation assays. FIG. 3C shows Annexin V binding as measured by flow cytometry analysis of control or DCV-treated LNCaP-ENR cells. FIG. 3D shows inhibition of LNCaP cell viability after treatment with enzalutamide, DCV, or the combination thereof. Here, the control value (i.e., results using only solvent, ~0.4% DMSO treatment), was deducted from each experimental values. Error bars show Standard Error (SE).  is $p<0.005$; * is $p<0.0005$.

FIG. 4A shows average tumor volumes of vehicle or DCV-treated animals (n=3 per group, $p<0.005$). Error bars represent standard deviation from the mean. FIG. 4B shows representative vehicle- and DCV-treated mice taken at 4 weeks of treatment. FIG. 4**C shows TRIB2 protein levels in vehicle and DCV-treated mouse tumors by IHC using monoclonal anti-Trib2 antibody.

FIG. 13 shows the amino acid sequence of Trib2 (SEQ ID NO: 1), including the residues that interact with DCV.

FIG. 14 depicts the flow cytometry results evaluating apoptosis in LNCaP-ENR cells treated with a control for 24 hours. Cells were stained with PerCP-Cy5.5 Annexin V.

DETAILED DESCRIPTION

Definitions

Figures 1B, 1C, 2A:
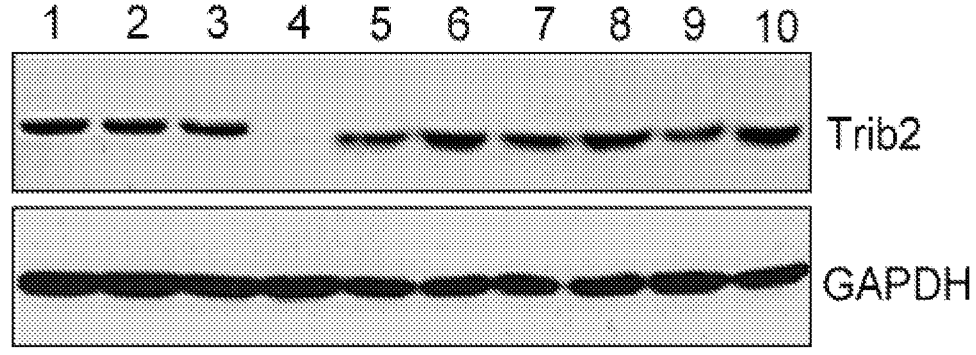

The term "combination" as used herein refers to the administration of two or more therapeutic agents. This term encompasses simultaneous, separate and/or sequential administration of therapeutic agents.

A "counterpart non-cancer cell" as used herein is a normal, non-transformed cell that is used as a reference to a cancer cell and is typically derived from the same tissue or progenitor cell as the cancer cell to which it is being compared. By contrast, a cell that has undergone malignant transformation is a cancer cell.

As used herein, the phrase "derived from" as it relates to a cell refers to the entity and/or location from which the cell originates. For example, a cell may be derived from a subject in that said cell is found in or taken from said subject. A cell may be derived from a subject by any methods known in the art, including collection of one or more cells by biopsy or by taking a blood sample. As another example, a cell may be derived from a specific organ or tissue in a subject. In a patient with cancer, a cancer cell may be derived from the patient, for instance, by methods including tumor biopsy. As another example, a cell that is differentiated may be derived from a less differentiated cell, such as a progenitor cell.

The term "express" as it relates to a cell or population of cells refers to gene expression or protein production by the cell or population of cells. As used herein, "express" or "expression" can refer to one or more of the following: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein. In some embodiments of the present disclosure, a protein may be over-expressed or expressed at higher levels in different cells. In some embodiments, a protein (e.g., TRIB2) may be over-expressed or expressed at higher levels in a cancer cell compared to a non-cancer cell, such as a counterpart non-cancer cell.

The terms "inhibit" or "inhibition of" mean to reduce or block by a measurable amount, or to reduce or block entirely. The term inhibition as used herein can refer to an inhibition or reduction of at least about 10%, at least about 15%, at least about 20%, at least about 25%, at least about 30%, at least about 35%, at least about 40%, at least about 50%, at least about 60%, at least about 70%, at least about 80%, at least about 90%, at least about 95%, or at least about 99%.

The term "prevention" as used herein refers to a prophylactic approach intended to substantially diminish the likelihood or severity of a condition or biological manifestation thereof, or to delay the onset of such condition or biological manifestation thereof.

As used herein, the term "subject" is intended to include human and non-human animals. The terms "subject" and "patient" are used interchangeably and can refer to human patients, as well as non-human primates or experimental animals such as rabbits, dogs, cats, rats, mice, and other animals. Preferred subjects of the present disclosure include human patients in need of a treatment for a disease or disorder. The compositions and methods described herein are suitable for the treatment of a subject having a disease or disorder that benefits from inhibition of Tribbles homolog 2 (TRIB2). A subject of the present disclosure may be a patient suffering from cancer, such as lung cancer and/or prostate cancer. In a particular embodiment, the compositions and methods described herein are particularly suitable for treatment of lung cancer, and/or prostate cancer, such as enzalutamide-resistant prostate cancer (ERPC).

As used herein, the term "therapeutically effective amount" refers to an amount that is sufficient to confer a desired biological or therapeutic result. A therapeutically effective amount of a therapeutic agent can treat, improve symptoms of, prevent, and/or delay the onset of a disease, disorder, and/or condition. In reference to cancer, a therapeutically effective amount may comprise an amount sufficient to cause a tumor to shrink and/or suppress tumor growth. A therapeutically effective amount may prevent or delay unwanted cell proliferation, delay tumor development, ameliorate symptoms, prolong survival or induce stabilization of the cancer or tumor. A therapeutically effective amount of a therapeutic agent or combination of therapeutic agents may result in one or more of the following: (i) reduce the number of cancer cells; (ii) reduce tumor size; (iii) inhibit, slow or stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. A therapeutically effective amount can be administered in one or more administrations. In some embodiments, a therapeutically effective amount is provided in a single dose. In some embodiments, a therapeutically effective amount is administered in a dosage regimen comprising a plurality of doses. One of ordinary skill in the art would be able to determine a therapeutically effective amount to treat a subject based on such factors as the subject's size, the severity of the subject's symptoms, and the particular composition or route of administration selected.

As used herein, the terms "treatment" or "treating" refer to an approach for obtaining a beneficial or desired result, preferably a beneficial or desired clinical result. Such beneficial or desired clinical results include, but are not limited to: (1) curing, healing, alleviating, relieving, altering, remedying, ameliorating, improving, interfering with, or affecting a condition (e.g., a disease), the symptoms of the condition, or the biological manifestations of the condition; (2) interfering with one or more points in the biological cascade that leads to or is responsible for the condition; (3) preventing, delaying or slowing the onset or progression of the symptoms, complications, biological manifestations, and/or biochemical indicia of a disease or condition; or (4) otherwise arresting or inhibiting further development of the disease, condition, or disorder. The compositions and methods of the present disclosure are suitable for obtaining beneficial or desired results such as reducing the proliferation of (or destroying) cancerous cells or other diseased cells, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals. Treatment can include administration of one or more therapeutic agents with the purpose to achieve the beneficial or desired results described herein.

The terms "tumor" and "cancer" are used interchangeably and refer to a cell or population of cells whose growth, proliferation or survival is greater than growth, proliferation or survival of a normal counterpart cell. The cell or population of cells in a tumor or cancer possess abnormal growth, and typically the growth is uncontrolled. The term "malignancy" refers to the property of a tumor or cancer cell to have the ability to invade nearby tissue. The term "metastasis" refers to spread or dissemination of a tumor, cancer or neoplasia to other sites, locations or regions within the subject, in which the sites, locations or regions are distinct from the primary tumor or cancer.

The terms "resistant" or "resistance" as used herein refer to the state in which (i) a disease or condition in a subject, or (ii) a cell or population of cells characterized by having the properties of a disease or condition, does not respond to a specified treatment. A subject suffering from a disease or condition may have a disease or condition with primary resistance, which means that the disease or condition does not respond at all to treatment. Alternatively, a subject may have a disease or condition with secondary resistance, which means that the disease or condition initially responds to treatment but develops resistance later on. A cell or population of cells may also have primary resistance or secondary resistance. A cell can be modified to be resistant to a specific treatment for research purposes. As used in the present disclosure, resistance refers to a cancer cell or population of cancer cells, either in isolation or in the context of a disease or condition in a subject suffering from the cancer, wherein the cancer cell or population of cancer cells do not respond to specified treatment As used herein, "about" means within acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" can mean range of up to 20%. When particular values are provided in the application and claims, unless otherwise stated, the meaning of "about" should be assumed to be within acceptable error range for that particular value.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

As used herein, "pharmaceutically acceptable carrier" or "pharmaceutical acceptable excipient" includes any material which, when combined with an active ingredient, allows the ingredient to retain biological activity and is non-reactive with the subject's immune system, and can include any and all solvents, diluents, carriers, dispersion media, coatings, antibacterial and antifungal agents, isotonic and absorption delaying agents, and the like that are physiologically compatible, non-toxic, and does not interfere with the mechanism of action of DCV or a pharmaceutically acceptable salt thereof, as would be known to one of ordinary skill in the art (see, for example, Remington's Pharmaceutical Sciences, 18th Ed. Mack Printing Company, 1990, pp. 1289-1329).

Preferably, the pharmaceutical acceptable excipient is suitable for intravenous, intramuscular, subcutaneous, parenteral, spinal or epidermal administration (e.g., by injection or infusion). Depending on the route of administration, DCV or a pharmaceutically acceptable salt thereof, may be coated in a material to protect the compound from the action of acids and other natural conditions that may inactivate the compound. Pharmaceutically acceptable excipients include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The methods of treatment of the disclosure comprise administering a safe and effective amount of a compound described herein or a pharmaceutically-acceptable salt thereof to a patient in need thereof.

"Such as" has the same meaning as "such as but not limited to." Similarly, "include" has the same meaning as "include but not limited to," while "including" has the same meaning as "including but not limited to."

The terms "tumor," "cancer" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumor, cancer or neoplasia to other sites, locations or regions within the subject, in which the sites, locations or regions are distinct from the primary tumor or cancer.

Additionally, unless otherwise stated, structures depicted herein are also meant to include compounds that differ only in the presence of one or more isotopically enriched atoms. Examples of isotopes that can be incorporated into compounds of the invention and pharmaceutically acceptable salts thereof include isotopes of hydrogen, carbon, nitrogen, oxygen, phosphorous, sulfur, fluorine, iodine, and chlorine, such as 2H, 3H, 11C, 13C, 14C, 15N, 170, 180, 31P, 32P, 35S, 18F, 36Cl, 123I and 125I.

DCV of the present invention and pharmaceutically acceptable salts of DCV that contain the aforementioned isotopes and/or other isotopes of other atoms are within the scope of the present invention. Isotopically-labelled compounds of the present invention, for example those into which radioactive isotopes, such as 3H and 14C, are incorporated, are useful in drug and/or substrate tissue distribution assays. Tritiated hydrogen (3H) and carbon-14 (14C) isotopes are particularly preferred for their ease of preparation and detectability. 11C and 18F isotopes are particularly useful in PET (positron emission tomography), and 125I isotopes are particularly useful in SPECT (single photon emission computerized tomography), all useful in brain imaging. Further, substitution with heavier isotopes such as deuterium (2H) can afford certain therapeutic advantages resulting from greater metabolic stability, for example increased in vivo half-life or reduced dosage requirements and may be preferred in some circumstances. Isotopically labeled compounds of the invention can generally be prepared by carrying out the procedures disclosed in the schemes and/or in the examples below, and substituting a readily available isotopically labeled reagent for a non-isotopically labeled reagent.

Unless otherwise stated, structures depicted herein are also meant to include all isomeric (e.g., enantiomeric, diastereomeric, and geometric (or conformational)) forms of the structure. "Isomer" refers to compounds that have the same composition and molecular weight but differ in physical and/or chemical properties; for example (Z) and (E) double bond isomers, and (Z) and (E) conformational isomers. The structural difference may be in constitution (geometric isomers) or in the ability to rotate the plane of polarized light (stereoisomers); for example, the R and S configurations for each asymmetric center. The compounds of the invention may contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof. Chiral centers may also be present in a substituent such as an alkyl group.

Where the stereochemistry of a chiral center present in DCV of the invention, or in any chemical structure illustrated herein, is not specified the structure is intended to encompass any stereoisomer and all mixtures thereof. Thus, compounds of the invention containing one or more chiral centers may be used as racemic mixtures, enantiomerically enriched mixtures, or as enantiomerically pure individual stereoisomers.

Individual stereoisomers of a compound of the invention which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

Unless otherwise stated, all tautomeric forms of the compounds of the invention are within the scope of the invention.

Any numerical range disclosed herein encompasses the and lower limits and each intervening value, unless otherwise specified. Other than in the working examples, or where otherwise indicated, numerical values (such as numbers expressing quantities of ingredients, reaction conditions) as used in the specification and claims are modified by the term "about". Accordingly, unless indicated to the contrary, such numbers are approximations that may vary depending upon the desired properties sought to be obtained. At the very least, and not as an attempt to limit the application of the doctrine of equivalents to the scope of the claims, each numerical parameter should be construed in light of the number of significant digits and ordinary rounding techniques.

While the numerical parameters setting forth the scope of the disclosed subject matter are approximations, the numerical values set forth in the working examples are reported as precisely as possible. Any numerical value, however, inherently contains certain errors necessarily resulting from the standard deviation found in its respective testing measurements.

Unless defined otherwise, the meanings of technical and scientific terms as used herein are those commonly understood by one of ordinary skill in the art to which the disclosed subject matter belongs.

Daclatasvir (referred to synonymously herein as "DCV") is an FDA-approved, orally available antiviral compound commonly used in combination with other antiviral agents to treat hepatitis C virus (HCV) infection Margusino-Framiñán, L., et. al. (2019) *Effectiveness and safety of daclatasvir/sofosbuvir with or without ribavirin in genotype 3 hepatitis C virus infected patients*. Results in real clinical practice. Rev Esp Quimioter. 32(2): 137-144. DCV has the official IUPAC name: 4,4'-bis[2-((2S)-1-{(2S)-2-[(methoxycarbonyl)amino]-3-methylbutanoyl}-2-pyrrolidinyl)-1H-imidazol-4-yl]-1,1'-biphenyl, CAS #1009119-64-5. The term "DCV" also includes pharmaceutically acceptable salts of DCV as defined and exemplified herein.

Treatment of Prostate Cancer

Globally, prostate cancer is the second most common cancer in men. Prostate cancer develops when the cells of prostate glands mutate and transform into cancer cells. Tumors form when the cancer cells divide uncontrollably and spread to surrounding prostate tissue. In some cases, a tumor continues to grow and spread from the primary site to different sites in the body, a process referred to as metastasis. Prostate cancer cells can invade nearby organs and may enter the bloodstream and lymphatic system. Common sites of metastasis for prostate cancer are bones and lymph nodes.

Clinical Evaluation and Management of Prostate Cancer

The initial evaluation of prostate cancer involves clinical staging to determine the extent of cancer spread. Clinical staging is important for risk stratification of disease, which helps clinicians assess disease prognosis.

Several tests are available for detection, diagnosis and risk stratification of prostate cancer. These include digital rectal examination, assessment of serum prostate-specific antigen (PSA), imaging, and biopsy. Imaging helps determine if the disease is regional or metastatic. A biopsy is used to confirm the diagnosis of prostate cancer. Genomic profiling and tissue-based molecular assays are also available for disease evaluation. In addition to these tests, other factors that are considered in the initial management and assessment of disease include patient age, life expectancy, overall medical condition, presence or absence of symptoms, and patient preferences for different treatment options.

A treatment plan for diagnosed prostate cancer may include management and/or definitive treatment. Management of prostate cancer involves active surveillance or watchful waiting. Active surveillance aims to prevent the spread of cancer and involves postponement of immediate therapy combined with careful surveillance. If, in the course of following active surveillance, there is evidence of increased risk of disease progression, definitive treatment can be initiated. Watchful waiting differs from active surveillance and involves the decision at the outset to forego definitive treatment and to provide systemic or local treatment to palliate symptoms. Definitive treatments for prostate cancer include surgery, radiation therapy, hormone therapy or chemotherapy. If disease has spread to the bones, other treatments are considered as part of care including pain medications, bisphosphonates and targeted therapy.

Risk stratification informs treatment decisions for prostate cancer. For clinically localized, very low-risk and low-risk prostate cancer, active surveillance may be an appropriate approach. For some patients, definitive therapy, including radical prostatectomy, brachytherapy, or radiation therapy, may also be appropriate. For example, definitive therapy may be initiated for a patient initially considered to have very low-risk disease if there is a high probability of disease progression or if there is evidence of progression. In both cases (clinically localized, very low-risk and clinically localized, low-risk prostate cancer), the decision of treatment approach considers risks and benefits of each treatment approach and patient's individual preferences. For clinically localized, intermediate-risk prostate cancer, radiation therapy and radical prostatectomy are both appropriate options. Active surveillance is offered as an option for patients with favorably intermediate-risk disease, but this option increases risk of developing metastases compared to definitive treatment. For higher risk prostate cancers that are clinically localized or locally advanced, treatment options include radiation therapy, brachytherapy, and hormonal therapy such as androgen deprivation therapy (ADT). For some patients with locally advanced and very high-risk prostate cancer, radical prostatectomy with extended lymph node dissection is also an option. Stage IV (metastatic) disease is classified if a patient has clinical lymph node involvement or disseminated metastases. Typical treatment for patients with clinical lymph node involvement is definitive radiation therapy and ADT. For disseminated disease, the initial treatment approach is usually hormonal therapy/ADT, which may be combined with chemotherapy, such as docetaxel.

Androgen Deprivation Therapy (ADT) for Treatment of Prostate Cancer

Androgen deprivation therapy (ADT) reduces levels of androgen hormones, such as testosterone, thereby targeting prostate cancer cells that rely on androgen hormones for growth. Surgical ADT involves surgical castration and is therefore considered an aggressive and permanent method of treatment. Pharmaceutical ADT includes chemical castration and treatment with antiandrogens. Chemical castration includes LHRH agonists and antagonists, both of which lower the amount of testosterone production. Examples of LHRH agonists and antagonists used in ADT include leuprorelin, goserelin, triptorelin, histrelin, buserelin, and degarelix. Antiandrogens work by blocking the body's ability to use androgens. For example, antiandrogens prevent binding of testosterone to androgen receptors. Binding of testosterone to androgen receptors found on prostate cells initiates signaling that promotes growth and maintains prostatic differentiation; however, these pro-growth signals are oncogenic in the context of cancer cells. Antiandrogens can also target testosterone synthesis and androgen receptor nuclear translocation. Examples of antiandrogens are enzalutamide, cyproterone acetate, flutamide, nilutamide, bicalutamide, abiraterone acetate, seviteronel, apalutamide, and darolutamide.

Enzalutamide-Resistant Prostate Cancer

Enzalutamide is a nonsteroidal antiandrogen (NSAA) medication indicated for the treatment of patients with castration-resistant prostate cancer (CRPC) and metastatic castration-sensitive prostate cancer (mCSPC). Enzalutamide acts as an androgen receptor inhibitor, and is considered to impinge on multiple steps of the androgen receptor signaling pathway in tumor cells. Although some patients show initial response to treatment, enzalutamide-resistant prostate cancer (ERPC) has been clinically documented.

ERPC is one of the most deadly form of malignancies, and is the cause of excruciating pain and suffering because of bone metastasis, and eventual death. Currently, there is no effective treatment available for ERPC and most prostate cancer deaths happen because of enzalutamide-resistant type of aggressive prostate cancer.

Tribbles Homolog 2 (TRIB2) as a Molecular Target for Enzalutamide-Resistant Prostate Cancer (ERPC)

Tribbles homolog 2 (TRIB2) is a pseudokinase encoded in humans by the TRIB2 gene. TRIB2 belongs to the mammalian Tribbles family of serine/threonine pseudokinases (TRIB2, TRIB2, and TRIB3) that have a catalytically impaired pseudokinase domain and show very low or no phosphotransferase activity. TRIB proteins are thought to act as scaffold proteins that mediate the ubiquitylation and subsequent proteasomal degradation of substrate proteins. In addition to their roles in the context of protein stability, TRIB proteins are also recognized to modulate the activity of signaling pathways such as the canonical AKT pathway.

Dysregulation of TRIB2 has been linked to a variety of malignancies, including leukemia, melanoma, lung cancer, and liver cancer. However, despite being implicated as an oncogenic protein, there is a lack of target-validated small-molecule compounds available to better understand the oncogenic mechanisms of and treatment opportunities related to TRIB2.

As described herein, TRIB2 is over-expressed and plays a critical role in the survival of enzalutamide-resistant type of prostate cancer (ERPC) cells. Inhibition of Trib2 by shRNA kills ERPC cells by triggering apoptosis. These observations and the examples of the present disclosure provide compelling motivation for pursuing TRIB2 as a new molecular target for the treatment of ERPC.

Provided in the present disclosure are tools, agents and methods that may be used for identifying TRIB2 inhibitors. As a non-limiting example, a high-throughput drug screen using existing small molecules in conjunction with a readout of TRIB2 levels and/or activity may be employed to identify inhibitors of TRIB2. Various cell lines may be used to identify TRIB2 inhibitors according to the provided methods, including cells modified to express a detectable version of TRIB2 protein or cells that normally express high levels of TRIB2 protein. Validation of hits from initial screening can be carried out to characterize and/or confirm efficacy of identified TRIB2 inhibitors. Examples of validation methods include immunoassays to detect TRIB2 levels, cell viability assays using cells that require TRIB2 function, and in vivo assays to determine effects of putative TRIB2 inhibitors on tumor cells that rely on TRIB2 function.

Repurposing the Antiviral Daclatasvir (DCV) for Prostate Cancer Therapy

Daclatasvir (DCV) Use in the Treatment of Hepatitis C Virus (HCV) Infection

Daclatasvir (DCV) is an FDA-approved, orally available antiviral compound commonly used in combination with other antiviral agents to treat hepatitis C virus (HCV) infection. DCV has the official IUPAC name: 4,4'-bis[2-((2S)-1-{(2S)-2-[(methoxycarbonyl)amino]-3-methylbutanoyl}-2-pyrrolidinyl)-1H-imidazol-4-yl]-1,1'-biphenyl, CAS #1009119-64-5. DCV is commercially available from Sigma-Aldrich Inc./Millipore-Sigma Product ID: ADV465749207-10MG, vendor SKU: 10310-10MG. (St. Louis MO, USA).

DCV inhibits the HCV non-structural protein 5A (NS5A) by direct binding. NS5A is important for HCV replication.

By inhibiting the activity of NS5A protein, DCV causes disruption of the viral RNA replication complex, blockage of viral HCV RNA production, and inhibition of viral replication. Other agents used in combination with DCV for HCV infection include sofosbuvir, which is an inhibitor of the viral RNA polymerase (NS5B protein) and ribavirin, which is a nucleoside analogue. DCV is contraindicated in combination with drugs that strongly induce CYP3A, including phenytoin, carbamazepine, rifampin, and St. John's wort.

The efficacy of DCV in combination with sofosbuvir and with or without ribavirin was evaluated in three phase 3 clinical trials, ALLY-1, ALLY-2 and ALLY-3. ALLY-1 evaluated DCV, sofosuvir and ribavirin in subjects with chronic HCV infection and Child-Pugh A, B, or C cirrhosis or HCV recurrence after liver transplantation. ALLY-2 evaluated DCV and sofosbuvir in subjects with chronic hepatitis C and HIV coinfection. ALLY-3 evaluated DCV and sofosbuvir in subjects with chronic HCV genotype 3 infection and compensated liver disease who were treatment naive or treatment experienced. Based on the ALLY-3 randomized, multicenter, open-label, active-controlled clinical trial, using 60 mg once daily oral dose for 12 weeks in 152 patients (NCT02319031), DCV was given approval for use in hepatitis C virus (HCV) infection in July of 2015.

Applications of Daclatasvir (DCV) as a Treatment for Cancer

The Applications of Daclatasvir (DCV) as a Treatment for Enzalutamide-Resistant Prostate Cancer (ERPC)

The present disclosure demonstrates that DCV can inhibit Tribbles homolog 2 (TRIB2). As discussed above, TRIB2 has been linked to a variety of malignancies, and, according to the present disclosure, is a proposed molecular target for enzalutamide-resistant prostate cancer (ERPC). Therefore, in accordance with the present disclosure, DCV treatment can be repurposed against TRIB2-overexpressing cancers, such as ERPC.

As shown herein, TRIB2 protein levels are reduced in DCV-treated versus control-treated human ERPC cells. DCV decreases the viability of ERPC cells and induces rapid apoptotic cell death. The observed reduction in TRIB2 protein levels and apoptotic death occur at micromolar concentrations of DCV. In contrast to ERPC cells, DCV shows minimal effects on normal, non-cancer cells under the same experimental conditions.

In one aspect, the present disclosure provides a method of preventing or treating cancer in a subject in need thereof, said method comprising administering a therapeutically effective amount of daclatasvir (DCV) to a subject suffering from cancer. In some embodiments, the present disclosure provides methods of preventing or treating cancer that over-expresses or has higher levels of expression of Tribbles homolog 2 (TRIB2). In some embodiments, the present disclosure provides methods of preventing or treating prostate cancer. Prostate cancer that may be treated according to the methods of the present disclosure include cancer that has previously been treated with androgen deprivation therapy (ADT) (e.g., enzalutamide), cancer that is resistant to ADT, or cancer that has previously been treated with ADT and developed resistance to ADT treatment. In some embodiments, DCV can be used in accordance with the present disclosure to treat enzalutamide-resistant prostate cancer (ERPC).

In some embodiments, DCV selectively attacks cancer cells (e.g., cancer cells that over-express TRIB2 and/or prostate cancer cells). In some embodiments, DCV minimally affects non-cancer cells. In some embodiments, DCV minimally affects cells which do not express or express low levels of TRIB2.

In some embodiments, compositions and methods of the present disclosure may be useful for reducing a tumor volume or burden in a subject, inhibiting tumor growth in a subject, or reducing the levels of TRIB2 protein in a tumor.

Pharmaceutically Acceptable Compositions and Formulations

DCV, or a pharmaceutically acceptable salt thereof, can be formulated as pharmaceutical compositions comprising a therapeutically or prophylactically effective amount of the compound or salt, and one or more pharmaceutically compatible (acceptable) ingredients. In some aspects, pharmaceutical compositions of DCV, or a pharmaceutically acceptable salt thereof, and pharmaceutical excipients are provided in which an effective amount of the compound or salt, is in admixture with the excipients, suitable for administration to a mammal. In preferred aspects, DCV, or a pharmaceutically acceptable salt thereof, is formulated for administration to a human. The present disclosure provides a pharmaceutical composition comprising DCV, or a pharmaceutically acceptable salt thereof, formulated for administration to a human subject in need thereof. The formulated composition comprising DCV, or a pharmaceutically acceptable salt thereof, will generally comprise one or more pharmaceutically compatible (acceptable) ingredients.

Exemplary pharmaceutical or non-pharmaceutical compositions typically include one or more carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable excipients include, for example, amino acids, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will typically contain a therapeutically effective amount of DCV, or a pharmaceutically acceptable salt thereof, in purified form, together with a suitable amount of carrier so as to provide the form for proper administration to the subject. The formulations correspond to the mode of administration.

The pharmaceutically acceptable carrier or vehicle can be particulate, so that the compositions are, for example, in tablet or powder form. The carrier(s) can be liquid, with the compositions being, for example, an oral syrup, flavored water, or injectable liquid.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant, and flavor enhancer. In some aspects, the composition is formulated into a powder and the end user mixes the power in aqueous solution for oral administration. In a composition for administration by injection (as described above), one or more of a surfactant, preservative, wetting agent, dispersing agent, suspending agent, buffer, stabilizer and isotonic agent can also be included.

The composition and preparation of capsules are well known in the art. For example, capsules may be prepared from gelatin (e.g., Type A, Type B), carrageenan (e.g., kappa, iota, lambda) and/or modified cellulose (e.g., hydroxypropyl methyl cellulose, methyl cellulose, hydroxypropyl methyl cellulose acetate succinate, hydroxypropyl methyl cellulose phthalate, cellulose acetate phthalate), and optionally one or more excipients such as oils (e.g., fish oil, olive oil, corn oil, soybean oil, coconut oil, tri-, di- and monoglycerides), plasticizers (e.g., glycerol, glycerin, sorbitol, polyethylene glycol, citric acid, citric acid esters such as triethylcitrate, polyalcohols), co-solvents (e.g., triacetin, propylene carbonate, ethyl lactate, propylene glycol, oleic acid, dimethylisosorbide, stearyl alcohol, cetyl alcohol, cetostearyl alcohol, glyceryl behenate, glyceryl palmitostearate), surfactants, buffering agents, lubricating agents, humectants, preservatives, colorants and flavorants. Capsules may be hard or soft. Examples of hard capsules include ConiSnap®, DRcaps®, OceanCaps®, Pearlcaps®, Plantcaps®, DUOCAP®, Vcaps®, and Vcaps®. Plus capsules available from Capsugel®. Hard capsules may be prepared, for example, by forming two telescoping capsule halves, filling one of the halves with a fill comprising DCV, or a pharmaceutically acceptable salt thereof, and sealing the capsule halves together. The fill may be in any suitable form, such as dry powder, granulation, suspension or liquid. Examples of soft capsules include soft gelatin (also called softgel or soft elastic) capsules, such as SGcaps®. Soft capsules may be prepared, for example, by rotary die, plate, reciprocating die or Accogel® machine method. In embodiments, the capsule may be a liquid-filled hard capsule or a soft-gelatin capsule.

Tablets can be made by compression or molding, optionally with one or more accessory ingredients. Compressed tablets can be prepared by compressing in a suitable machine DCV or pharmaceutically acceptable salt thereof in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide sustained, extended, delayed or controlled release. Methods of formulating such sustained, extended, delayed or controlled release compositions are known in the art and disclosed in issued U.S. patents, including but not limited to U.S. Pat. Nos. 4,369,174, 4,842,866, and the references cited therein. Coatings, for example enteric coatings, can be used for delivery of compounds to the intestine (see, e.g., U.S. Pat. Nos. 6,638,534, 5,217,720, 6,569,457, and the references cited therein). In addition to tablets, other dosage forms, such as capsules, granulations and gel-caps, can be formulated to provide sustained, extended, delayed or controlled release.

In one embodiment, the pharmaceutical composition is formulated for parenteral administration. Examples of a pharmaceutical composition suitable for parenteral administration include aqueous sterile injection solutions and non-aqueous sterile injection solutions, each containing, for example, anti-oxidants, buffers, bacteriostatic agents and/or solutes that render the formulation isotonic with the blood of the intended recipient; and aqueous sterile suspensions and non-aqueous sterile suspensions, each containing, for example, suspending agents and/or thickening agents. The formulations can be presented in unit-dose or multi-dose containers, for example, sealed ampules or vials, and can be stored in a freeze dried (lyophilized) condition requiting only the addition of a sterile liquid carrier, such as water, immediately prior to use. In one embodiment, the pharmaceutical composition is formulated for intravenous administration.

In some embodiments, the pharmaceutical composition further includes a pharmaceutically acceptable excipient. A pharmaceutically acceptable excipient may be any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Remington: The Science and Practice of Pharmacy, 21.sup.st Ed. (Lippincott Williams & Wilkins, Baltimore, Md., 2005). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropyl methylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of DCV, or a pharmaceutically acceptable salt thereof, the manner of administration, the composition employed, and the severity of the disease or condition being treated.

In addition to administering the compound as a raw chemical, the compounds of the disclosure may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the disclosure may be administered to any patient which may experience the beneficial effects of the compounds of the disclosure. Foremost among such patients are mammals, e.g., humans, although the disclosure is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present disclosure are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this disclosure are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present disclosure. Various modifications and alterations of the compositions and methods described above can readily be achieved using expertise available in the art and are within the scope of the disclosure.

Methods of Treatment

In some embodiments of the present disclosure, DCV, or a pharmaceutically acceptable salt thereof, can be employed under a variety of conditions and therapeutic uses to treat a variety of immunological conditions, including cancer.

The dose to be administered to a subject in need thereof may vary depending upon a variety of factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, size, condition, general health, the prior medical history of the patient being treated, target disease, the purpose of the treatment, conditions, the immunogenicity of the entity, and the accessibility of the target cells in the biological matrix and the like. When the combination of the present disclosure is used for treating various conditions and diseases directly or indirectly associated with immune checkpoints, in an adult subject, it is advantageous to intravenously or subcutaneously administer the antibody of the present disclosure.

In various embodiments, the appropriate dose of the active agents described herein is made by the clinician, e.g., using parameters or factors known or suspected in the art to affect treatment or predicted to affect treatment. In some embodiments, sound medical practice will dictate that the initial dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced, tissue damage, or estimated activity or stage in a cancer disease course. In some embodiments, the actual dosage levels of the active ingredients in the pharmaceutical compositions of the present disclosure may be varied so as to obtain an amount of the active ingredient which is effective to achieve the desired therapeutic response for a particular subject, composition, and mode of administration, without being toxic to the patient.

Compositions comprising the combination of the disclosure can be administered to the subject, for example, a human subject by one or more administration modalities, for example, continuous infusion, or by doses at intervals of, e.g., one day, one week, or 1-7 times per week. Doses may be provided parenterally, for example, intravenously, or subcutaneously.

By way of illustration only, and taking into consideration various factors for determining appropriate doses and dosing frequencies, an exemplary dose of DCV, or a pharmaceutically acceptable salt thereof, to be administered to a patient in need thereof can include a single dose of DCV, or a pharmaceutically acceptable salt thereof) about 0.01 to about 100 mg/kg body weight, more preferably about 0.02 to about 7, about 0.03 to about 5, or about 0.05 to about 3 mg/kg body weight dosed, once or more times per day, and/or one or more times per week, for example, for one to four weeks, or one to eight weeks, or one to twelve weeks, or one to fourteen weeks.

In some embodiments, an exemplary dosing regimen can include administration of a maximal dose or dosing frequency that avoids significant undesirable side effects. In some embodiments, a total weekly dose of each active agent of the combination, independently may be at least 0.05 μg/kg body weight, at least 0.2 μg/kg, at least 0.5 μg/kg, at least 1 μg/kg, at least 10 μg/kg, at least 100 μg/kg, at least 0.2 mg/kg, at least 0.5 mg/kg, at least 1.0 mg/kg, at least 2.0 mg/kg, at least 10 mg/kg, at least 15 mg/kg, at least 20 mg/kg, at least 25 mg/kg, or at least 50 mg/kg, or at least or at least 100 mg/kg. In another example, an illustrative dose of each active agent of the combination of the disclosure, to be administered to a patient in need thereof may be about 0.001 mg/kg to about 200 mg/kg of the patient's body weight.

The dosage to a subject in need thereof, may be between 0.001 mg/kg and 200 mg/kg, 0.001 mg/kg and 100 mg/kg, 0.001 mg/kg and 50 mg/kg, 0.001 mg/kg and 25 mg/kg, 0.001 mg/kg and 10 mg/kg, 0.001 mg/kg and 5 mg/kg, 0.001 mg/kg and 1 mg/kg, 0.001 mg/kg and 0.5 mg/kg and any dosage amount there between. As non-limiting examples, treatment according to the present disclosure may be provided as a daily dosage of an each active agent of DCV, or a pharmaceutically acceptable salt thereof, in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Depending on the severity of the condition, and the various factors discussed herein, the dose, frequency and the duration of the treatment can be adjusted accordingly, in view of proper medical standards known to those of skill in the art. In certain exemplary embodiments, each active agent of the combination of the disclosure can be administered as an initial dose of at least about 0.1 mg to about 800 mg, about 1 to about 500 mg, about 5 to about 300 mg, or about 10 to about 200 mg, to about 100 mg, or to about 50 mg. The first dose of one or both active agents of the combination may be an initial loading dose, to be followed subsequently by a plurality of maintenance doses.

In certain exemplary embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks, or doses of the combination of the disclosure may be repeated and the administrations may be separated by at least 1 day, 2 days, 3 days, 5 days, 10 days, 15 days, 30 days, 45 days, 2 months, 75 days, 3 months, or at least 6 months.

The route of administration of the compositions containing DCV, or a pharmaceutically acceptable salt thereof, may be independently administered, or administered as a combination in a single formulation by, e.g., topical or cutaneous application, injection or infusion by intravenous, intraperitoneal, subcutaneous, intracerebral, intramuscular, intraocular, intraarterial, intradermal, intracerebrospinal, intralesional, subcuticular, intraarticular, subcapsular, subarachnoid, intraspinal, epidural and intrasternal injection and infusion, or by sustained release systems or an implant. The injectable preparations may include dosage forms for intravenous, subcutaneous, intracutaneous and intramuscular injections, drip infusions, etc. Numerous reusable pen and autoinjector delivery devices have applications in the subcutaneous delivery of a pharmaceutical composition of the present disclosure.

Examples include, but certainly are not limited to AUTOPEN™ (Owen Mumford, Inc., Woodstock, UK), DIS-ETRONIC™ pen (Disetronic Medical Systems, Burghdorf, Switzerland), HUMALOG MIX 75/25™ pen, HUMA-LOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nor-disk, Copenhagen, Denmark), BD™ pen (Becton Dickinson, Franklin Lakes, N.J.), OPTIPEN™, OPTIPEN PRO™ OPTIPEN STARLET™, and OPTICLIK™ (Sanofi-Aventis, Frankfurt, Germany), as exemplary pen based delivery methods contemplated herein in the administration of the present combination. Illustrative examples of pen based devices having applications in subcutaneous delivery of a pharmaceutical composition of the present disclosure include, the SOLOSTAR™ pen (Sanofi-Aventis), the FLEXPEN™ (Novo Nordisk), and the KWIKPEN™ (Eli Lilly).

Generally, the oral dosage of DCV, or a pharmaceutically acceptable salt, prodrug, or solvate thereof, or an enantiomer, a mixture of enantiomers, a mixture of two or more diastereomers, or an isotopic variant thereof, administered to an animal, for example a human subject, is about 0.001 mg/kg to about 100 mg/kg of the animal's body weight, more typically about 0.1 mg/kg, 1 mg/kg, 5 mg/kg, 10 mg/kg, 25 mg/kg, 50 mg/kg, 100 mg/kg, 150 mg/kg, 200 mg/kg, 250 mg/kg, or 300 mg/kg to about 500 mg/kg of the animal's body weight. In some aspects, the dosage of DCV, or a pharmaceutically acceptable salt, prodrug, or solvate thereof, or an enantiomer, a mixture of enantiomers, a mixture of two or more diastereomers, or an isotopic variant thereof, administered to animal is about 1 mg, about 5 mg, or about 10 mg to about 350 mg per day, or from about 1 mg, about 5 mg, about 10 mg, about 15 mg or about 20 mg to about 100 mg per day.

DCV, or a pharmaceutically acceptable salt or solvate thereof, or an enantiomer, a mixture of enantiomers, a mixture of two or more diastereomers, or an isotopic variant thereof, can be administered on a daily, weekly, biweekly or monthly schedule, according to the desired effect. In some aspects DCV, or a pharmaceutically acceptable salt thereof, can be administered from about 1 to 5, about 1 to about 10, about 1 to about 15, or more cycles, wherein each cycle is a month in duration. The doses within each cycle can be given on daily (including once daily, twice daily, or more than twice daily), every other day, twice weekly, weekly, bi-weekly, once every three weeks or monthly basis. A cycle may optionally include a resting period. Alternatively, a resting period can be included between cycles. In some aspects, administration will be for the duration of the disease.

As described herein, the amount of DCV, or a pharmaceutically acceptable salt, prodrug, or solvate thereof, or an enantiomer, a mixture of enantiomers, a mixture of two or more diastereomers, or an isotopic variant thereof, that is effective in the methods described herein will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

Compositions within the scope of this disclosure include all compositions wherein DCV, or a pharmaceutically acceptable salt thereof, is contained in an amount which is effective to achieve its intended purpose. While individual needs vary, determination of optimal ranges of effective amounts of each component is within the skill of the art. Typically, DCV, or a pharmaceutically acceptable salt or solvate thereof, prodrug, or an enantiomer, a mixture of enantiomers, a mixture of two or more diastereomers, or an isotopic variant thereof, may be administered to mammals, e.g. humans, orally at a dose of 0.0025 to 100 mg/kg, or an equivalent amount of the pharmaceutically acceptable salt thereof, per day of the body weight of the mammal being treated for the cancer being treated. In one embodiment, about 0.01 to about 25 mg/kg is orally administered to treat, ameliorate, or prevent such disorders. For intravenous injection or infusion injection, the dose of the checkpoint inhibitor antibody or antigen binding fragment thereof would be about 0.1 to about 1000 mg/kg, or from about 0.1 mg/kg to about 500 mg/kg patient weight.

The unit oral dose of DCV, or a pharmaceutically acceptable salt or solvate, prodrug, thereof, or an enantiomer, a mixture of enantiomers, a mixture of two or more diastereomers, or an isotopic variant thereof, may comprise from about 0.01 mg to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, DCV, or a pharmaceutically acceptable salt, prodrug, or solvate thereof, or an enantiomer, a mixture of enantiomers, a mixture of two or more diastereomers, or an isotopic variant thereof, may be present at a concentration of about 0.01 to 100 mg per gram of carrier. In a one embodiment, the compound is present at a concentration of about 0.07-1.0 mg/mL, for example, about 0.1-0.5 mg/mL, and in one embodiment, about 0.4 mg/mL.

The present disclosure may be used to treat a neoplastic disease, such as solid or non-solid cancers. As used herein, "treatment" encompasses the prevention, reduction, control and/or inhibition of a neoplastic disease. Such diseases include TRIB2-positive cancer cells, including ERPC cells and TRIB2-positive lung cancer, including but not limited to: non-small cell lung cancer, small cell lung cancer, oat cell cancer, adenocarcinoma, squamous cell carcinoma, large cell (undifferentiated) carcinoma, papillary carcinoma, adenosquamous carcinoma, carcinoid tumors, adenoid cystic carcinomas lymphomas, and sarcomas, and sarcomatoid carcinoma. In various embodiments, the lung cancers described in the foregoing are TRIB2-positive lung cancers. The present disclosure provides an effective method for treating TRIB2-positive cancer, such as prostate cancer, in particular, ERPC, and/or lung cancer by administering a therapeutically effective amount of daclatasvir (DCV) to a subject in need thereof.

Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. Cancers that may be treated according to the disclosure include but are not limited to cells or neoplasms of the lung and prostate The tumor may be metastatic or a malignant tumor. TRIB2-positive cancer cells, including ERPC cells and TRIB2-positive lung cancer, including but not limited to: non-small cell lung cancer, small cell lung cancer, oat cell cancer, adenocarcinoma, squamous cell carcinoma, large cell (undifferentiated) carcinoma, papillary carcinoma, adenosquamous carcinoma, carcinoid tumors, adenoid cystic carcinomas lymphomas, and sarcomas, and sarcomatoid carcinoma. In various embodiments, the lung cancers described in the foregoing are TRIB2-positive lung cancers. The present disclosure provides an effective method for treating TRIB2-positive cancer, such as prostate cancer, in particular, ERPC, and/or lung cancer by administering a therapeutically effective amount of daclatasvir (DCV) to a subject in need thereof.

In some embodiments, the neoplastic disease to be treated is lung cancer, prostate cancer and prostate cancer. Most preferably, the neoplastic disease to be treated is TRIB2-positive cancer cells, including ERPC cells and TRIB2-positive lung cancer, including but not limited to: non-small cell lung cancer, small cell lung cancer, oat cell cancer, adenocarcinoma, squamous cell carcinoma, large cell (undifferentiated) carcinoma, papillary carcinoma, adenosquamous carcinoma, carcinoid tumors, adenoid cystic carcinomas lymphomas, and sarcomas, and sarcomatoid carcinoma.

Combination Therapies

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethimide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 2 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 2

| Exemplary antineoplastic agents approved for use in the U.S | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d] pyrimidin-4-one monosodium salt) | Zyloprim | GlaxoSmithKline, Research Triangle Park, NC |
| Altretamine (N,N,N',N',N",N",-hexamethyl-1,3,5-triazine-2, 4, 6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin A2 and bleomycin B2) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0, 0']-, (SP-4-2)) | Paraplatin | Bristol-Myers Squibb |
| Carmustine (1,3-bis(2-chloroethyl)-1-nitrosourea) | BCNU, BICNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-y1] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine | Cytoxan, Neosar | Bristol-Myers Squibb |

TABLE 2-continued

| Exemplary antineoplastic agents approved for use in the U.S | | |
|---|---|---|
| 2-oxide monohydrate) | | |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S )-3-Acetyl-1,2,3,4,6,11-hexahydro-3,5,12-trihydroxy-10-methoxy-6, 11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4, 7b, 10b, 13a-hexahydroxytax-11-en-9-one 4-acetate 2-benzoate, trihydrate) | Taxotere | Aventis Pharmaceuticals, Inc., Bridgewater, NJ |
| Doxorubicin HC1 (8S,10S)-10-[(3-amino-2,3,6-trideoxy-á-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | nolone Dromosta | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |

TABLE 2-continued

| Exemplary antineoplastic agents approved for use in the U.S | | |
|---|---|---|
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5, 12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4, 11-diethyl-4-hydroxy-9-[(4-piperi-dinopiperidino)carbonyloxy]-1H-pyrano[3', 4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[(2amino-5-formy11,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HC1 ((-)-( S)-2,3,5, 6-tetrahydro-6-phenylimidazo [2,1-b] thiazole monohydrochloride $C_{11}H_{12}N_2S$•HCl) | Ergamisol | Janssen Research Foundation, Titusville, NJ |

TABLE 2-continued

| Exemplary antineoplastic agents approved for use in the U.S | | |
|---|---|---|
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoy 1]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5ß, 20-Epoxy-1,2a, 4,7ß, 10ß, 13a-hexahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, \|Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-u-(2-methylhydrazino)-p-toluamide monohydrochloride) | Matulane | Sigma Tau Pharmaceuticals, Inc., Gaithersburg, MD |
| Quinacrine | Atabrine | Abbott Labs |

TABLE 2-continued

| Exemplary antineoplastic agents approved for use in the U.S | | |
|---|---|---|
| (6-chloro-9-( 1-methyl-4-diethyl-amine) butylamino-2-methoxyacridine) | | |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b )-D-glucopyranose and 220 mg citric acid anhydrous) | Zanosar | Pharmacia & Upjohn Company |
| Talc ($Mg_3Si_4O_{10}$ (OH)2) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranosidel) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3', 4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-buteny1]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG2a lambda anti-CD20 antibody (I 131 is a radioimmunotherapeutic antibody)) | Bexxar | Corixa Corp., Seattle, WA |
| Trastuzumab (recombinant monoclonal IgG? kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5, 12-trihydroxy-7 methoxy-6,11-dioxo-[[4 2,3,6-trideoxy-3-[(trifluoroacetyl)-amino-a-L-lyxo-hexopyranosyl]oxyl]-2-naphthacenyl]-2-oxoethyl pentanoate) | Valstar | Anthra--> Medeva |
| Vinblastine, Leurocristine ($C_{46}H_{56}N_40_{10}$•$H_2SO_4$) | Velban | Eli Lilly |
| Vincristine ($C_{46}H_{56}N_40_{10}$•$H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |

TABLE 2-continued

| Exemplary antineoplastic agents approved for use in the U.S | | |
|---|---|---|
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasentan, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, lumiliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphyrins, cisplatin, mitomycin, tirapazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects.

Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

EXAMPLES

Example 1. High-Throughput Screening for Identification of Compounds that Downregulate TRIB2

The present example demonstrates identification of daclatasvir (DCV) as an inhibitor of Tribbles homolog 2 (TRIB2).

A high-throughput screen (HTS) was performed with 1600 compounds selected from a collection of marketed drugs (Catalog No.: HY-L022, Medchem Express, Monmouth Junction, NJ). The screening also included additional compounds from Selleck Chemicals (Houston, TX), Sigma Chemicals (St. Louis, MO), Cayman Chemicals (Ann Arbor, MI), Santa Cruz Biotech (Santa Cruz, CA), and IndoFine Chemicals (Hillsborough, NJ).

Human foreskin fibroblast cells (HFF) cells were transfected with a Trib2-Luciferase (Luc-Trib2) fusion construct. Cells were plated in 96-well tissue culture plates and treated with compounds (10 μM) for 24 hours. Luciferase activity was measured using an EnduRen™ Live cell substrate kit (commercially available from PROMEGA CORP.®, Madison, WI). Daclatasvir showed more than 70% inhibition of Trib2-luciferase activity (FIG. 1A and FIG. 1B). By contrast, another antiviral compound, ledipasvir (LDV) showed no inhibition in the same assay (FIG. 1A and FIG. 1C). For further development, selected compounds were counter-screened with control luciferase-transfected HFF cells. Daclatasvir also passed counter-screen tests, where DCV is screened with only luciferase and without Trib2; this shows that DCV does not inhibit luciferase activity directly.

These results demonstrate that DCV inhibits TRIB2 in a luciferase fusion protein-based assay and suggest that DCV may be a new inhibitor of TRIB2 protein. The inhibitory effects of DCV on Trib2-luciferase activity were not observed for other antiviral drugs, such as ledipasvir (LDV). Both DCV and LDV are used for the treatment of hepatitis C virus (HCV) infection. Like DCV, LDV is also an inhibitor of the hepatitis C virus (HCV) non-structural protein 5A (NS5A). Differences in the effects of DCV versus LDV in this example indicate that the inhibitory effects of DCV on TRIB2 protein may be specific to this compound and are not generally observed for all HCV antiviral drugs.

Example 2. Validation of Novel TRIB2 Inhibitors Using ERPC Cells

The present example demonstrates that daclatasvir, but not another antiviral drug, down-regulates TRIB2 protein levels and reduces viability of ERPC cells.

Enzalutamide-resistant prostate cancer (ERPC) cells (LNCaP-ENR cells) were plated and treated with 10 μM each of various compounds for 24 hours. Exemplary methods for developing and using LNCaP-ENR cells is disclosed in Monga, J., Subramani, D., Bharathan, A., and Ghosh, J. (2020) "Pharmacological and genetic targeting of 5-lipoxygenase interrupts c-Myc oncogenic signaling and kills enzalutamide-resistant prostate cancer cells via apoptosis." Scientific Reports 10: 6649, the disclosure of which is incorporated herein by reference in its entirety. Whole cell lysate proteins were analyzed by Western blot. TRIB2 antibody was used to detect protein levels of TRIB2 and GAPDH was used as loading control. Monoclonal anti-Trib2 antibody was purchased from Santa Cruz Biotech, Santa Cruz, CA. TRIB2 protein levels were downregulated by daclatasvir, but not by another antiviral drug ledipasvir (LDV) (FIG. 2A).

Figure 2B:
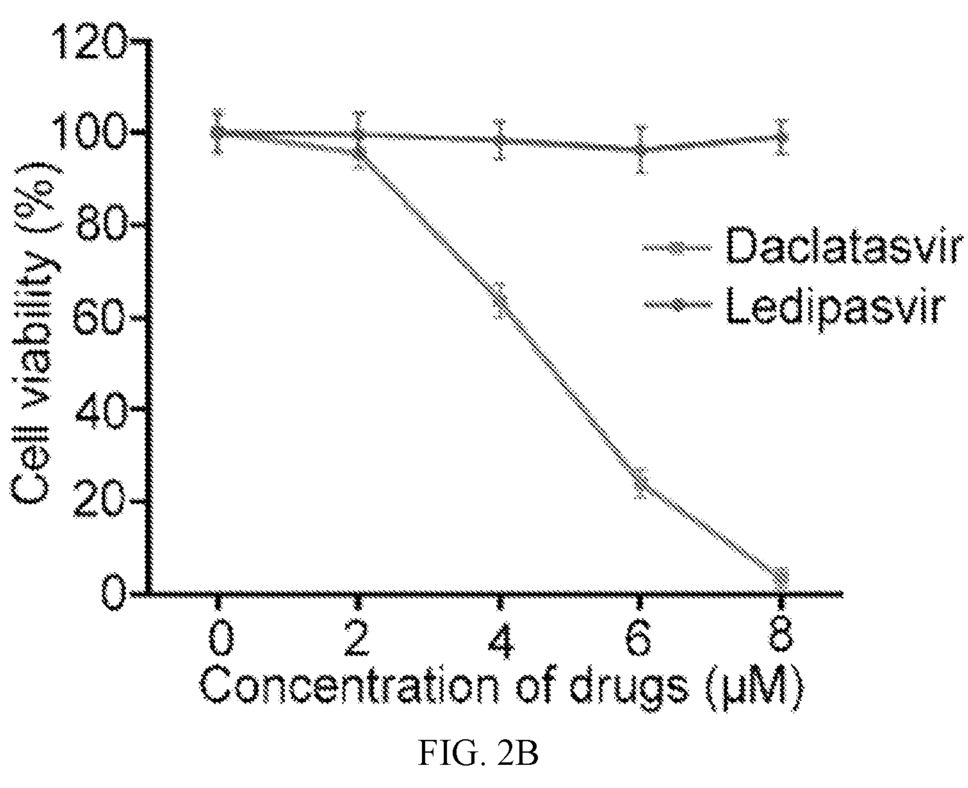

For viability assays, LNCaP-ENR cells (2,000 cells per well) were plated in 96 well plates in complete growth medium (RPMI plus 10% FBS) and treated with varying doses of DCV or LDV. Plates were incubated for 72 hours at 37° C. in a $CO_2$ incubator. Cell viability was measured by MTS/PES cell titer assay (Promega Corp., Madison, WI). Cell viability was effectively decreased by daclatasvir, but not by ledipasvir (FIG. 2B).

These results show that DCV can inhibit TRIB2 and can reduce the viability of ERPC cells at micromolar concentrations. Reduced levels of TRIB2 protein in DCV-treated cells may be an indication that DCV triggers the degradation of TRIB2 protein. The effects of DCV on downregulating TRIB2 protein levels and decreasing viability of ERPC cells mimic the effects of TRIB2 shRNA (unpublished data). Ledipasvir (LDV), another antiviral drug, neither downregulates TRIB2 nor kills ERPC cells, suggesting that the selective effect of DCV against TRIB2 protein is due to its structural difference.

Example 3. In Vitro Anti-Tumor Effects of DCV

The present example demonstrates anti-tumor effects of DCV treatment in prostate cancer cells.

Figure 3A:
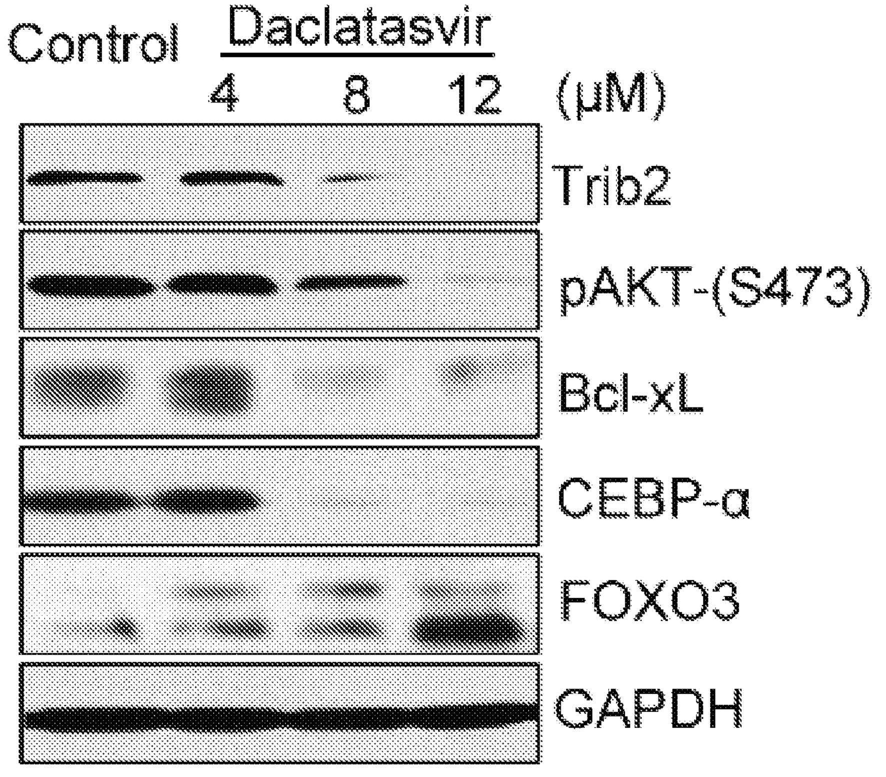
FIG. 3A-FIG. 3D show in vitro treatment effects of DCV in TRIB2-positive tumor cells.

LNCaP-ENR cells were treated with varying doses (4 μM, 8 μM, or 12 μM) of DCV for 24 hours. Effects on TRIB2 protein levels and its downstream targets (e.g., pAkt, Bcl-xL, Survivin, and FOXO3) were analyzed by Western blot. GAPDH was used as loading control. Protein levels of TRIB2, pAKT (S473), Bcl-xL, and Survivin were reduced in cells treated with 12 μM of DCV compared to control-treated cells (FIG. 3A). Levels of FOXO3 protein were increased at 12 μM of DCV treatment compared to control treatment. This was expected, as FOXO3 level is known to be decreased by Trib2. These effects on cellular protein levels were DCV concentration-dependent, with the most pronounced effects observed at the highest concentration tested (12 μM).

Figure 3B:
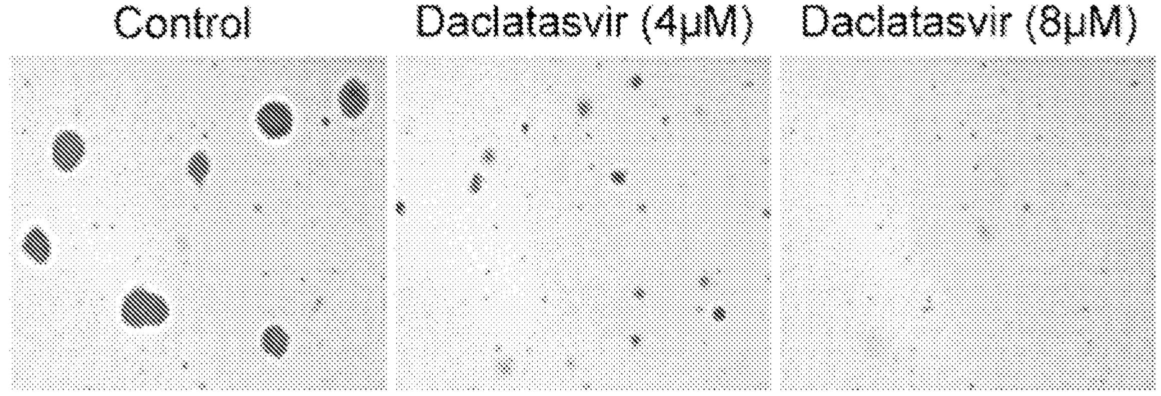

Effect of DCV on soft-agar colony formation was also analyzed. LNCaP-ENR cells (10,000 per well in 6-well plates) were plated in 0.3% soft-agar on top of a base layer of 0.6% agar. The cells were treated with DCV and incubated at 37° C. for three weeks in the $CO_2$ incubator. Cells were given fresh media and drug every fourth day. At the end of the incubation period, colonies were stained with 0.025% crystal violet, and pictures of colonies were taken with a Nikon digital camera at ×200. Image processing was done using Q-Capture Pro-7 software. Exemplary methods of the foregoing technique can be found in Sarveswaran, Sivalokanathan et al. "Inhibition of 5-lipoxygenase downregulates stemness and kills prostate cancer stem cells by triggering apoptosis via activation of c-Jun N-terminal kinase." *Oncotarget* vol. 10, 4 424-436. 11 Jan. 2019, the disclosure of which is incorporated herein by reference in its entirety. DCV at 8 μM completely blocked soft-agar colony formation (FIG. 3B).

Figure 3C:
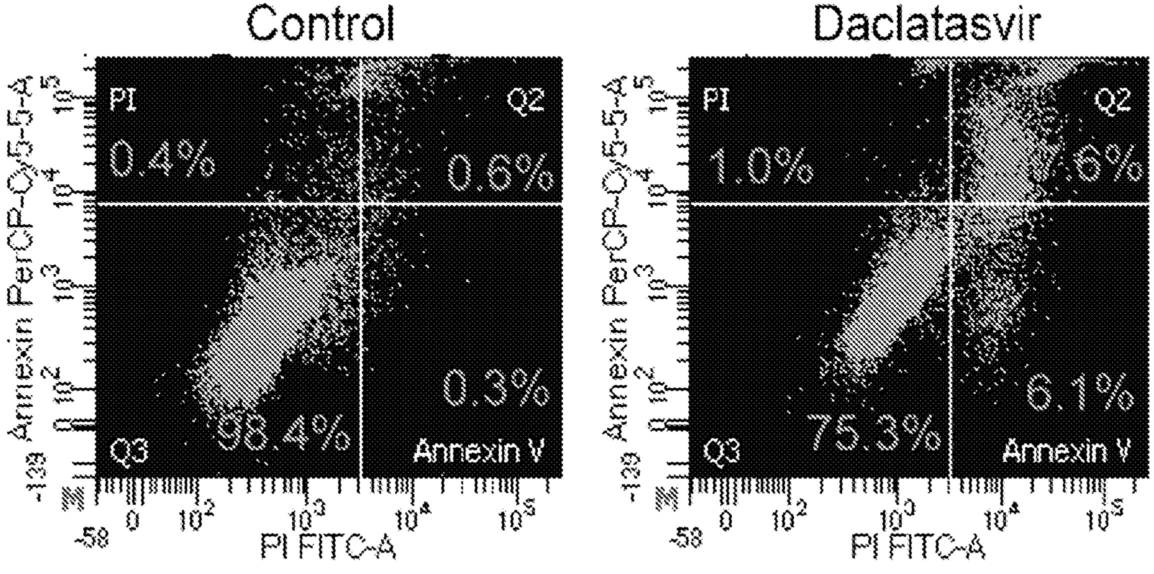

To test DCV effects on cancer cell apoptosis, LNCaP-ENR cells were treated with 8 μM DCV for 24 hours and analyzed by flow cytometry. Treatment with DCV indicated increased Annexin V binding, a read-out for apoptosis (FIG. 3C).

Figure 3D:
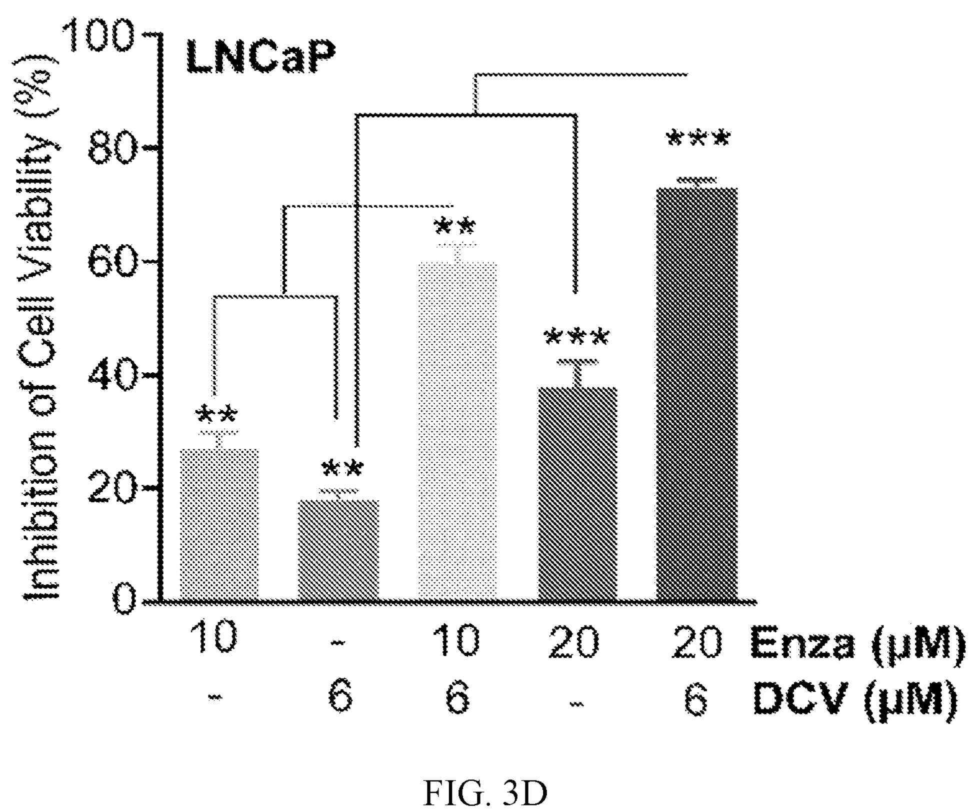

To assess the effects of DCV treatment alone and in combination with enzalutamide in prostate cancer cells, cell viability assays were performed using the LNCaP cell line. LNCaP cells are androgen-sensitive human prostate adenocarcinoma cells that respond to enzalutamide treatment. Cells were treated with enzalutamide (10 μM or 20 μM); DCV (6 μM), or the combination of enzalutamide and DCV for 72 hours and analyzed by MTS/PES assay. Combination treatment with enzalutamide and DCV showed synergistic effects on inhibition of cell viability compared to treatment with each drug alone (FIG. 3D).

These results show that treatment of TRIB2-positive tumor cells with DCV induced tumor cell apoptosis and reduced protein levels of TRIB2 protein and downstream targets of TRIB2, such as pAkt and Bcl-xL. In the soft-agar assay, an in vitro test of tumorigenicity, DCV blocked colony formation by ERPC cells. Complete inhibition of colony formation by ERPC cells signifies that DCV can penetrate to overcome tumor resistance due to compactness and hypoxic environment at the core of the lumpy mass of ERPC cells. Additionally, the present example shows that combination treatment with DCV and enzalutamide synergistically inhibits viability of prostate cancer cells that otherwise respond to enzalutamide monotherapy. Together, these results indicate that DCV could be an effective therapeutic for the treatment of aggressive, enzalutamide-resistant, lethal prostate cancer.

Example 4. In Vivo Anti-Tumor Effect of DCV

The present example demonstrates that in vivo treatment with DCV inhibits ERPC tumor growth in a murine xenograft model.

BALB/c nude mice were subcutaneously injected with the LNCaP-ENR cells ($1\times10^6$ cells per mouse) to develop tumors. Once the tumors reached a size of ~100 cubic mm, the mice were treated with 30 mg/kg/day DCV or a solution of DMSO:cremophor:PBS at 1:1:8 ratio, orally for four weeks (n=3). Tumor size and body weights were measured once per week. Tumor volumes were calculated using the following formula:

$$TV = a \times \frac{(b)^2}{2} \qquad \text{Formula (I)}$$

Wherein "TV" means tumor volume;

"a" is the long diameter of a tumor; and

"b" is the short diameter of a tumor.

Tumor samples were collected at 4 weeks post-treatment, and TRIB2 protein levels in the tumors were determined by immunohistochemistry (IHC) using monoclonal anti-Trib2 antibody (Santa Cruz Bio, Santa Cruz, CA; Cat. No.: 100878) at 1:100.

Figure 4A:
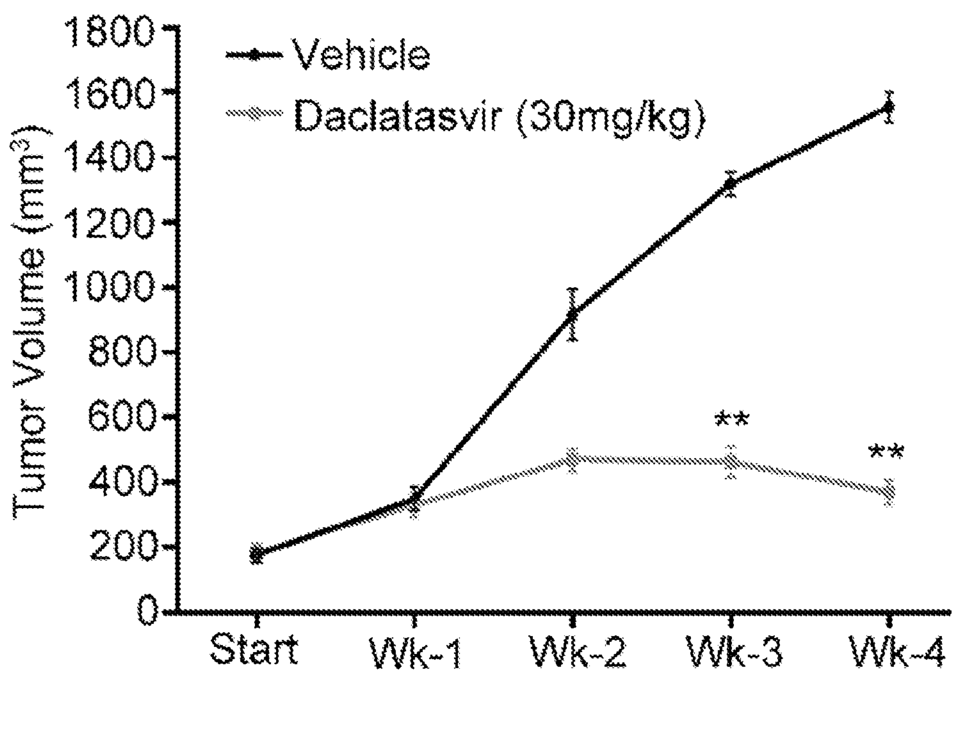
FIG. 4A-FIG. 4C show results of an in vivo xenograft study with DCV treatment of ERPC tumors in BALB/c nude mice.
Figure 4B:
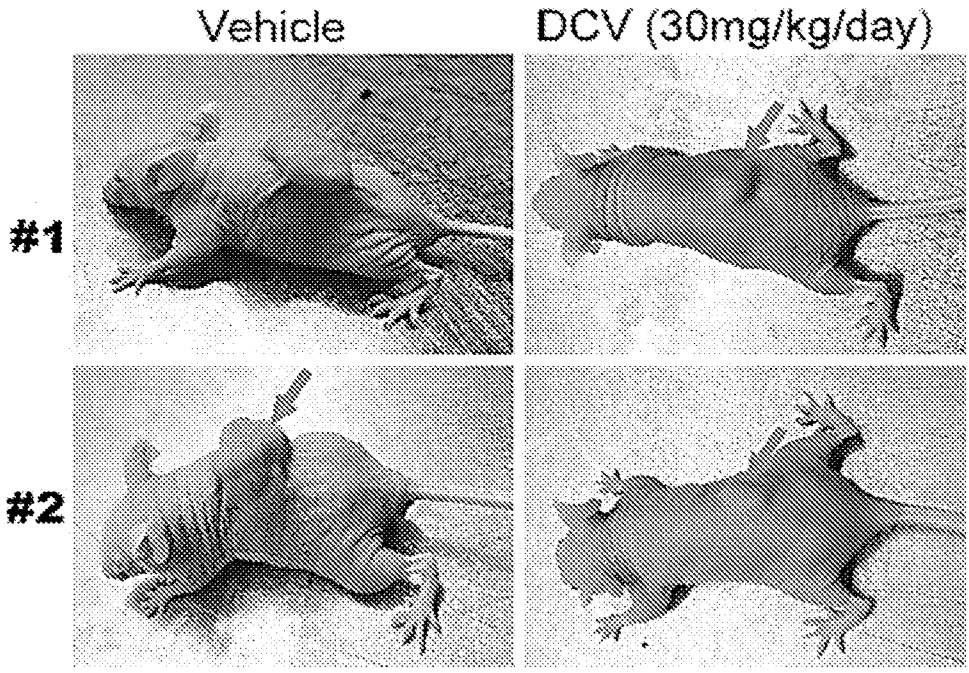
Figure 4C:
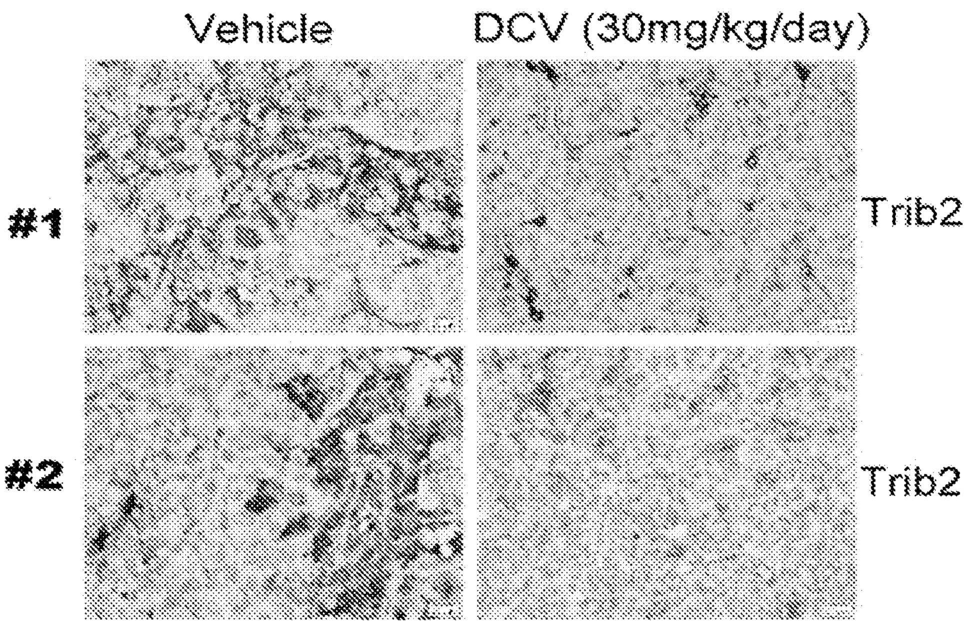

Tumor volumes of animals treated with DCV were significantly reduced compared to vehicle-treated animals (FIG. 4A and FIG. 4B). Additionally, tumors from DCV-treated animals indicated reduced TRIB2 protein levels by IHC (FIG. 4C). No sign of overt toxicity (significant loss of animal body weight, or change in locomotion, food intake, skin color, diarrhea, color of urine, general viscera) was observed with DCV treatment for four weeks.

These results show that DCV at 30 mg/kg/day (maximum tolerated dose (MTD) of DCV: >200 mg/kg/day) reduced TRIB2 protein levels in tumors and inhibited ERPC tumor growth in nude mice without any overt toxicity to animal health. Accordingly, DCV shows promising in vivo anti-tumor activity for TRIB2-positive tumors and could provide a new treatment for ERPC.

Example 5. Daclatasvir, an Antiviral Drug, Inhibits Tribbles 2 Pseudokinase and Kills Enzalutamide Resistant Prostate Cancer Cells Via Apoptosis FDA-approved enzalutamide is commonly prescribed to reduce growth of advanced prostate cancer by blocking androgen receptor function. However, even after initial good response, enzalutamide-resistant prostate cancer (ERPC) invariably develops which frequently progresses to widespread metastatic disease and becomes lethal. Much of the morbidity and mortality due to prostate cancer happens because of prostate cancer progression beyond anti-androgenic therapies. Management of ERPC poses special problem not only because available therapeutic regimen cannot effectively kill ERPC cells but also due to their propensity to invade large bones. Mechanism behind enzalutamide-resistance is not properly understood, which is delaying development of newer agents to overcome enzalutamide resistance. The present disclosure demonstrates that the Tribbles 2 pseudokinase is overexpressed in prostate cancer cells and tumors upon enzalutamide treatment. Forced expression of Tribbles 2 enhances prostate cancer cell growth and confers complete resistance to physiological doses of enzalutamide, suggesting that Trib2 plays an important role in the development and progression of ERPC. Though Trib2 has emerged as an excellent molecular target, suitable inhibitors are not commercially available for effective targeting. By designing a luciferase-tagged Trib2 fusion protein-based screening assay, the present disclosure demonstrates that daclatasvir, an antiviral drug, strongly inhibits Trib2-luciferase activity. The present disclosure also demonstrates that DCV degrades Trib2 proteins by direct binding and re-sensitizes ERPC cells. Because DCV is already FDA-approved and well-tolerated in humans, the findings presented herein indicate that DCV may emerge as a promising new agent for development of an effective therapy for advanced, enzalutamide-resistant type prostate cancer.

The inventor developed an in vitro model by chronically treating human LNCaP and MDA-PCA-2B prostate cancer cells with gradually increasing doses of enzalutamide (up to 30 μM) to mimic the clinical conditions in long-term enzalutamide therapy. Comprehensive gene expression analysis of the resultant enzalutamide-resistant cells revealed that the pseudokinase, Trib2, is overexpressed in enzalutamide-resistant cells compared to parental enzalutamide-sensitive cells (FIG. 1, A and B). Moreover, overexpression of Trib2 was also found in enzalutamide treated PDX tumors and patient prostate tumors. Inhibition of Trib2 effectively kills ERPC cells, suggesting that a targeted therapy can now be developed by inhibiting Trib2. However, because of its non-enzymatic nature and absence of any deep pocket, specific targeting of Trib2 by blocking its protein-protein interaction is extremely difficult. Thus, in spite of being recognized as a bona fide promoter for anti-androgenic therapy-resistant prostate cancer, Trib2 remains as an elusive molecular target for developing strategies to overcome Enzalutamide-resistance.

The main hurdle to develop agents to inhibit Trib2 is the lack of a quick and easy assay procedure to effectively screen large number of compounds. To overcome this problem, the present disclosure provides a design for a new assay system to measure the active state of Trib2 protein. The present disclosure describes a Trib2-luciferase gene construct by combining the full length human Trib2 gene with the luciferase gene from Renilla. Destabilization of the three-dimensional conformation of the resultant Trib2-luc fusion protein can deliver reportable outcome via alteration in the enzymatic activity of luciferase. A second screen was designed to eliminate compounds that affects the activity of only luciferase. Using this dual screen assay system, a library of 1600 FDA-approved compounds was screened, revealing that daclatasvir (DCV), an anti-viral drug, strongly inhibits the Trib2-luciferase activity. Later, it was found that though DCV inhibits the activity of Trib2-luciferase, it does not inhibit luciferase activity when Trib2 is not attached as fusion protein. The present disclosure also found that DCV directly binds and destabilizes pure Trib2 protein and decreases the half maximum melting temperature (Tm). Moreover, it was found that DCV downregulates Trib2 protein level in a range of aggressive cancer cell lines, including prostate, lung, and kidney. Thus, the luciferase-based assay system (involving first screen and a counter-screen) of the present disclosure emerges as an effective way to identify Trib2-targeting drugs using simple gene transfected cell lines in culture.

Results

High-Throughput Screening Identified DCV as a Novel Agent to Downregulate Tribbles 2.

The amino acid sequence in Trib2 protein bears similarity to a standard kinase and binds ATP, but it lacks a strong kinase activity (pseudokinase). Thus, the present disclosure provides a design for an assay system by combining full length human Trib2 gene with the luciferase gene from Renilla to make a fusion construct. To preserve the critical C-terminus of Trib2 protein, the luciferase gene was placed upstream of the Trib2 gene so that the luciferase component stayed at the N-terminus. Here, it was observed that the resultant fusion construct translates into a protein product of the size of ~72 kDa with strong luciferase activity.

After screening a range of established cell lines it was found that the human foreskin fibroblasts (HFF) do not express detectable Trib2 protein. Thus, the present disclosure transfected HFF cells with the luciferase tagged Trib2 gene construct. Cells were selected for overexpression of the fusion gene by two rounds of drug (G418) selection. The resultant cells (HFF-Trib2-Luc) were used to screen a library of about 1600 FDA-approved compounds (#HY-L022) purchased from Medchem Express (Monmouth Junction, NJ). Drug effects were tested in 96-well tissue culture plates following a standardized 24-hour assay protocol. The assays of the present disclosure revealed that about 1% of the compounds can inhibit Trib2-luc activity by 70% or more. Interestingly, the present disclosure found that daclatasvir downregulates luciferase activity in the first screen by 74%. (Table 3, FIG. 5). Moreover, DCV does not inhibit control luciferase activity in the second screen, suggesting that the effect of DCV may be because of its interaction with Trib2. Some other antiviral compounds were also tested, such as Ledipasvir (LDV), darunavir and dolutegravir which were completely ineffective to inhibit Trib2-luciferase activity in the same experimental system, indicating that a critical structural component/configuration is the key to inhibit Trib2 rather than a generalized antiviral property of the compounds. From the effects of unknown compounds revealed in the Trib2-luciferase fusion protein-based assay, the hit rate in the screening was found to be ~1%.

TABLE 3

Depicts the effects of a representative set of 104 FDA-approved compounds on Trib2-Luciferase fusion construct-transfected HFF cells are shown here. Cells were treated with the compounds disclosed herein (10 μM), for 24 hours, and luciferase activity was then measured using a kit from Promega Corp. (Madison, WI). For further development selected compounds are counter-screened with control luciferase-transfected HFF cells. Note: Daclatasvir showed more than 70% inhibition of Trib2-luciferase activity in 24 hours and passed counter-screen tests.

| Compound | Luciferase activity (%) | Compound | Luciferase activity (%) |
|---|---|---|---|
| Dichlorphrnamide | 100 | Darunavir | 93 |
| Ranolazine | 100 | Niraparib tosylate | 93 |
| 6-Acetamidohexanoic | 100 | Clofibric acid | 87 |
| Alcaftadine | 100 | Ajamaline | 93 |
| Temsirolmus | 94 | Sulfamethizole | 94 |
| Oxaceprol | 100 | Fimasartan | 88 |
| Mianserin | 55 | Anagrelide | 92 |
| Dolutegravir | 100 | Nadifloxacin | 96 |
| Nilotinib | 99 | Ponatinib | 42 |
| Efonidipine | 98 | Valnemulin | 83 |
| Dirithromycin | 100 | Mozavaptan | 86 |
| Clebopride | 100 | Dipyridamole | 98 |
| Ibudilast | 85 | Lansoprazole | 78 |
| Ramelteon | 100 | Atropine | 67 |
| Chlormerazanoine | 100 | Olmesartan | 80 |
| Famotidine | 100 | Estrone | 82 |
| Busulfan | 100 | Hydroxyfasudil | 46 |
| Epalrestat | 53 | Sulfaguanidine | 84 |
| Ornipressin | 27 | Prazosin | 49 |
| Ampiroxicam | 28 | Tigecycline | 63 |
| Droperidol | 100 | Doxorubicin | 28 |
| Nilvadipine | 89 | Ledipasvir | 100 |
| Triamterene | 100 | Levocarnitine | 84 |
| Methacholine | 99 | Sulfadiazine | 70 |
| Doxycycline | 91 | Guanfacine | 100 |
| Alprenolol | 91 | Tavaborole | 75 |
| Niclosamide | 62 | Isosorbide | 91 |
| Irinotecan | 85 | Betamipron | 87 |
| Fenofibrate | 92 | Udenafil | 100 |
| Ethambutol | 98 | Milnacipran | 85 |
| Gadodiamide | 89 | Carbidopa | 92 |
| Teniposide | 70 | Imipramine | 86 |
| Vincamine | 80 | Telotristat etiprate | 94 |
| Pemirolast | 88 | Trimetazidine | 100 |
| Cromolyn | 93 | Ronidazole | 100 |
| 5-Aminosalicyclic acid | 84 | Malathion | 91 |
| Tamibarotene | 100 | Danofloxacin | 81 |
| Dapoxetine | 88 | Azasetron | 100 |
| Telbivudine | 91 | Plerixafor | 93 |
| Mexiletine | 86 | Meloxicam | 100 |
| Noscapine | 100 | Tegafur | 100 |
| Efavirenz | 89 | Terconazole | 82 |
| Penciclovir | 97 | Dabrafenib | 72 |
| Tebipenem pivoxil | 100 | Triamcinolone | 72 |
| Venetoclax | 184 | Vorapaxar | 59 |
| Chlorambucil | 96 | Proparacaine | 88 |
| Resperine | 91 | Erlotinib | 50 |
| Clarithromycin | 97 | Daclatasvir | 28 |
| Etomidate | 100 | Pyridostigmine | 76 |
| Dexrazoxane | 100 | Fingolimod | 80 |
| Paroxetine | 93 | Minaprine | 79 |
| Penfluridol | 71 | Ticarcillin | 87 |
| Fluocinonide | 78 | Budesonide | 83 |

Figure 5:
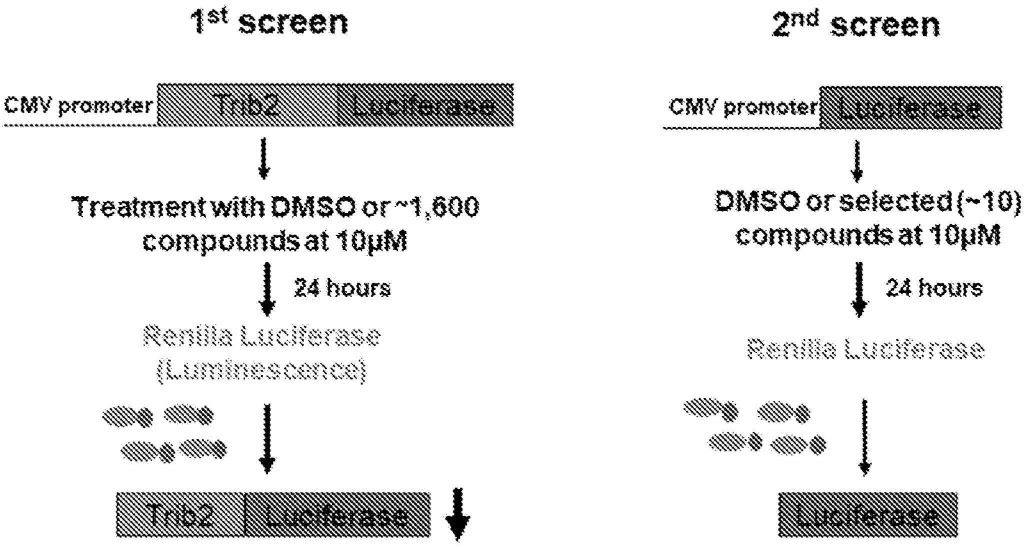
FIG. 5 depicts the screening strategy used to select compounds based on inhibition of luciferase activity in Trib2-Luc cells, but not in Luc cells. Compounds screened included a representative set of 104 FDA-approved compounds on Trib2-Luciferase fusion construct-transfected HFF cells are shown here. Cells were treated with compounds (10 μM) for 24 hours and measured luciferase activity using a kit from Promega Corp. (Madison, WI). For further development selected compounds are counter-screened with control luciferase-transfected HFF cells. Note: Daclatasvir showed more than 70% inhibition of Trib2-luciferase activity in 24 hours and passed counter-screen tests.

The screening strategy used to select compounds is shown in FIG. 5. Here, the screening strategy used to select compounds based on inhibition of luciferase activity in Trib2-Luc cells, but not in Luc cells. Compounds screened included a representative set of 104 FDA-approved compounds on Trib2-Luciferase fusion construct-transfected HFF cells are shown here. Cells were treated with compounds (10 μM) for 24 hours and measured luciferase activity using a kit from Promega Corp. (Madison, WI). For further development selected compounds are counter-screened with control luciferase-transfected HFF cells. Note: Daclatasvir showed more than 70% inhibition of Trib2-luciferase activity in 24 hours and passed counter-screen tests.

DCV Downregulates Trib2 Protein Level Via Proteasomal Degradation.

The present disclosure demonstrates that DCV (#4) efficiently down-regulates Trib2 protein level and decreases the viability of ERPC cells (FIG. 2A, 2B), mimicking the effects of Trib2 shRNA. DCV is known to inhibit the hepatitis C viral protein (NS5A) by direct binding. In the assays presented here, it was found that DCV inhibits Trib2 at micromolar doses, but Ledipasvir (LDV, #7), another anti-viral drug neither downregulates Trib2 nor kills ERPC cells, suggesting that the selective effect of DCV against Trib2 protein is due its structural difference. The present disclosure also showed that DCV dramatically decreases the in vitro invasion through extracellular matrix by both LNCaP-ENR and MR49F ERPC cells (data not shown). The present disclosure also found that DCV completely blocks the anchorage-independent colony-forming abilities of ERPC cells on soft-agar (FIG. 3B). Thus, Trib2 inhibitor drugs can stop the invasion and recolonization which are characteristics of advanced cancer phenotype (FIG. 3B; see Example 3). To verify the effects of DCV its effect on Trib2 downstream markers was analyzed, which revealed that DCV inhibits the protein levels of pAKT, Bcl-xL and survivin, and increased the level of FOXO3. Thus, the effect of DCV conforms with published reports of well-known Trib2 inhibitors. Accordingly, the findings of the present disclosure validate DCV as a new compound to inhibit the effect of Trib2 and thus can be used against ERPC cells and tumors which overexpress Trib2. Interestingly, ledipasvir which was used in parallel experiments was found to be completely ineffective to block invasion or soft-agar colony formation by the ERPC cells, which suggests for a highly selective effect of DCV in these processes.

Figure 6:
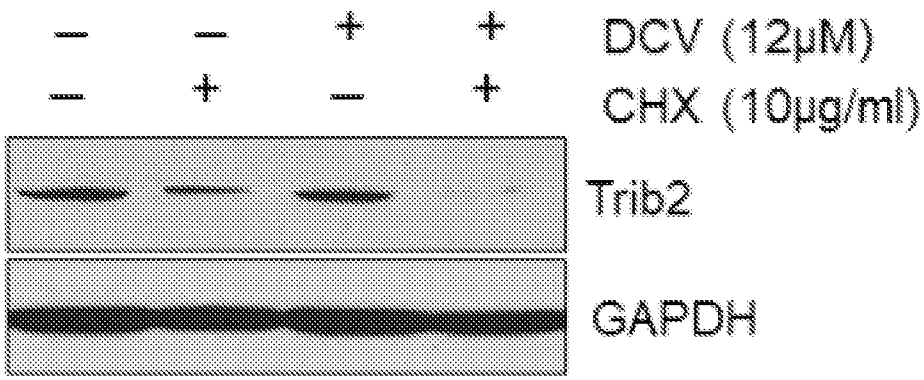
FIG. 6 depicts a Western blot showing the effect of (1) DCV (12 μM); or cycloheximide (CHX) (10 μg/mL) on Trib2 protein levels in LNCaP-ENR cells. GAPDH was used as a control. A "+" and/or "–" over each lane indicates the presences or absence of DCV or CHX, respectively.

FIG. 6 depicts a Western blot showing the effect of (1) DCV (12 μM); or cycloheximide (CHX) (10 μg/mL) on Trib2 protein levels in LNCaP-ENR cells. GAPDH was used as a control. A "+" and/or "−" over each lane indicates the presences or absence of DCV or CHX, respectively.

Figure 7:
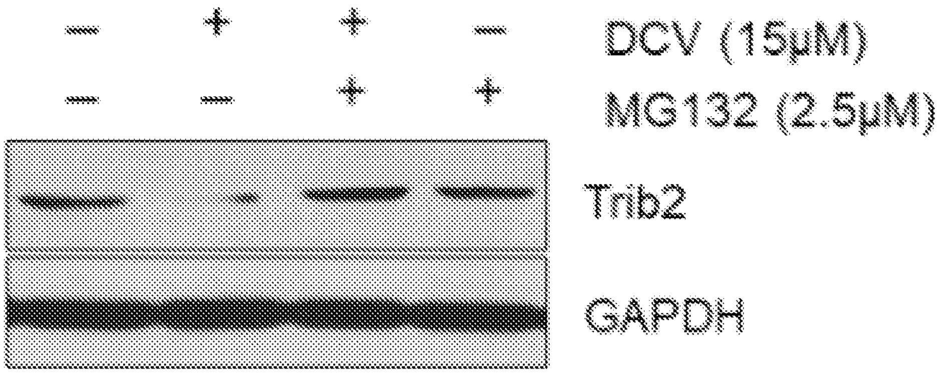
FIG. 7 depicts a Western blot showing the effect of (1) DCV (15 μM); or (2) $C_{26}H_{41}N_3O_5$ (CAS No. 133407-82-6) (Benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl]carbamate) ("MG132") (2.5 μM) on Trib2 protein levels in LNCaP-ENR cells. GAPDH was used as a control. A "+" and/or "–" over each lane indicates the presences or absence of DCV or CHX, respectively.

FIG. 7 depicts a Western blot showing the effect of (1) DCV (15 μM); or (2) $C_{26}H_{41}N_3O_5$ (CAS No. 133407-82-6) (Benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl]carbamate) ("MG132") (2.5 μM) on Trib2 protein levels in LNCaP-ENR cells. GAPDH was used as a control. A "+" and/or "−" over each lane indicates the presences or absence of DCV or CHX, respectively.

DCV Directly Binds and Destabilizes Trib2 Protein

Figure 8:
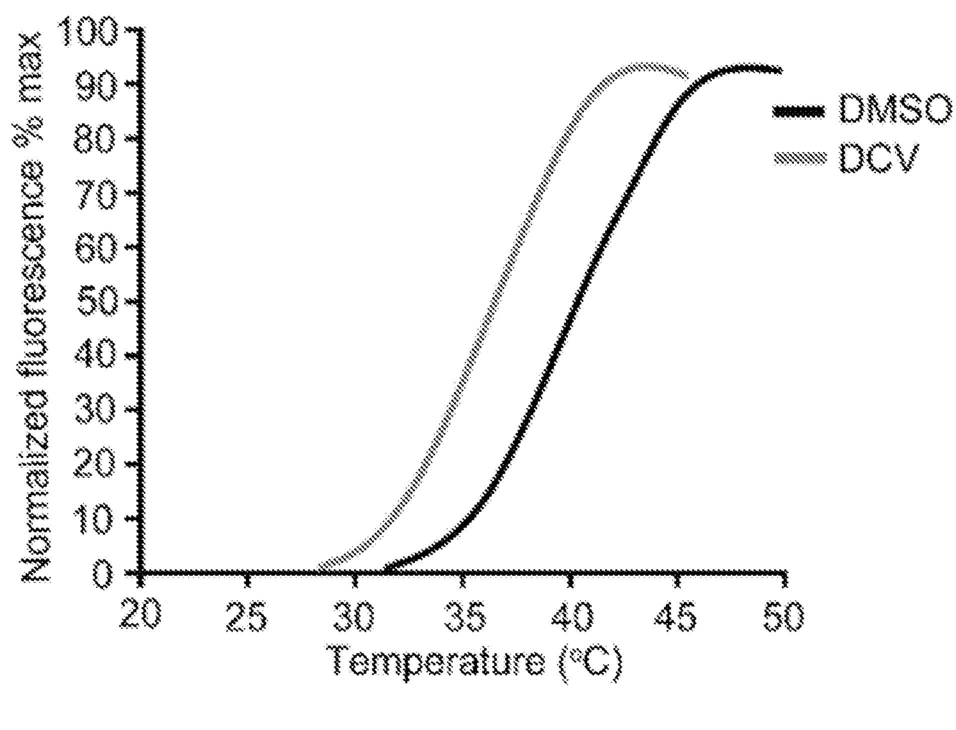
FIG. 8 depicts a graph showing the results of a thermal shift assay of pure Trib2 protein by Differential Scanning Spectro-fluorometry. Here, the results show that DCV shifts the melting curve of Trib2 to the left. And, the Tm decreased from 41° C. to 37° C., suggesting destabilization of protein by DCV.

Thermal shift assay of isolated Trib2 protein showed that DCV shifts the melting curve of Trib2 to the left. The Tm decreased from 41° C. to 37° C. (FIG. 8). The Swiss-Prot computer modeling using complete amino acid sequence of the human Trib2 protein revealed five amino acids to interact with DCV. These are: Arg-132, Ser-133, Glu-194, Glu-197, and Asp-198. The model suggests that DCV non-covalently binds and destabilizes Trib2 protein.

Figure 9:
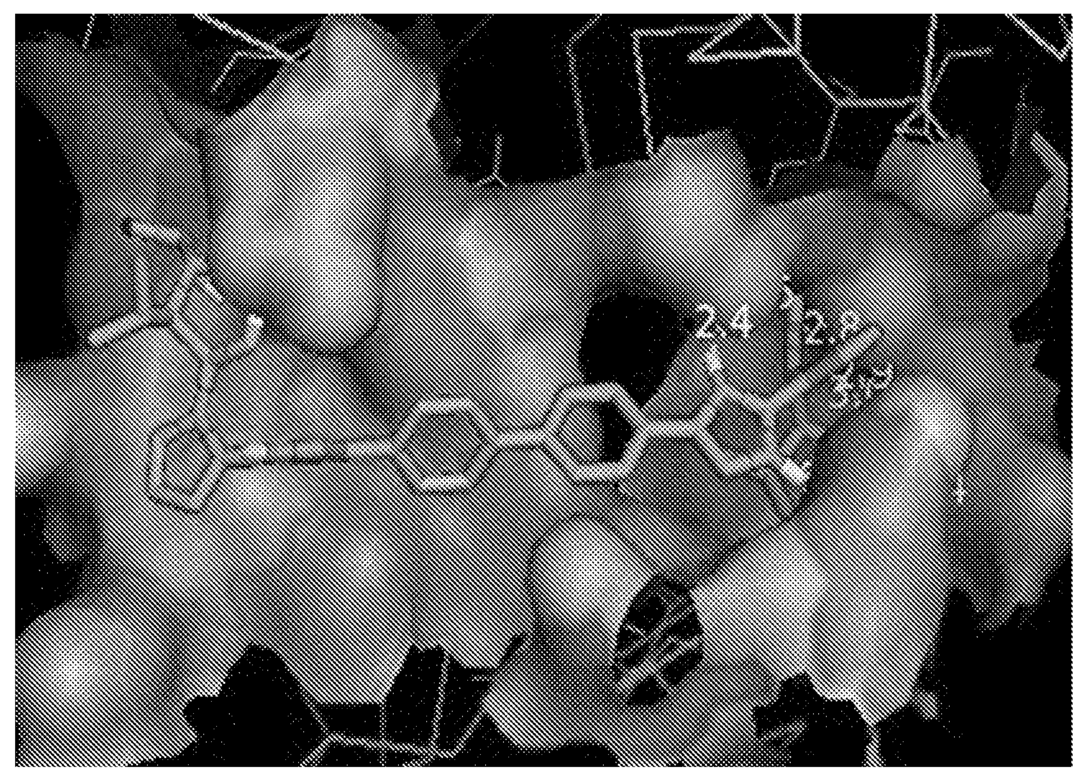
FIG. 9 shows the results of a molecular docking analysis of Trib2 (protein) and daclatasvir (ligand), presented in a 3D view.
Figure 10:
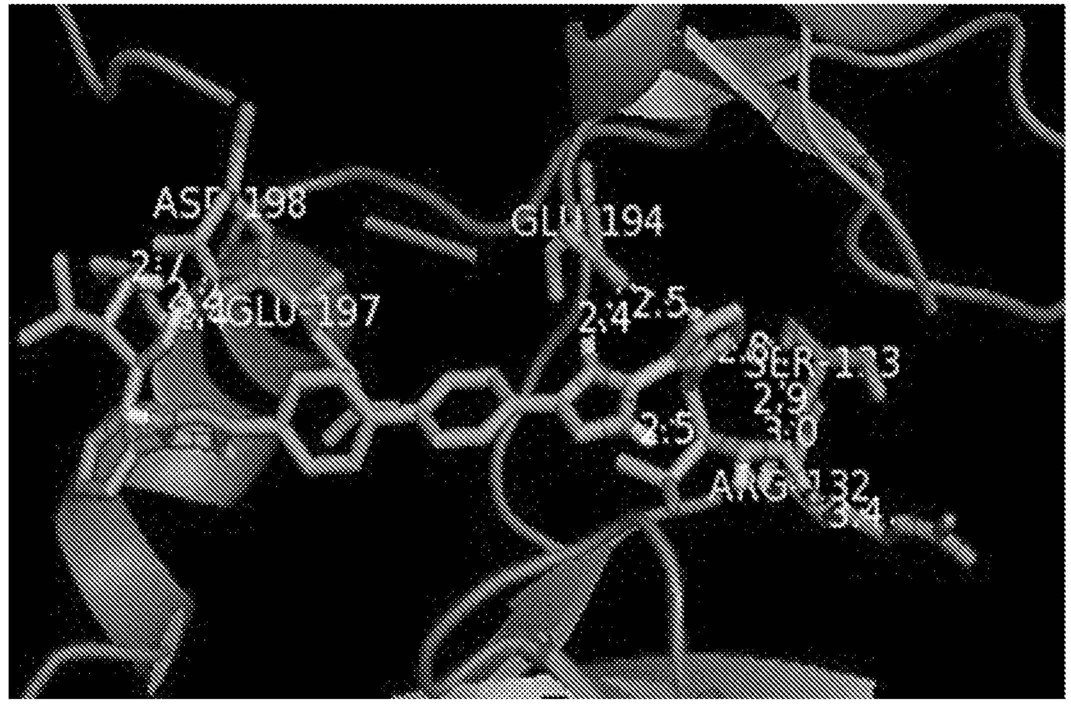
FIG. 10 shows the results of a molecular docking analysis of Trib2 (protein) and daclatasvir (ligand), presented in a view highlighting the secondary structures of Trib2 and amino acids Arg-132, Ser-133, Glu-194, Glu-197, and Asp-198.
Figure 11:
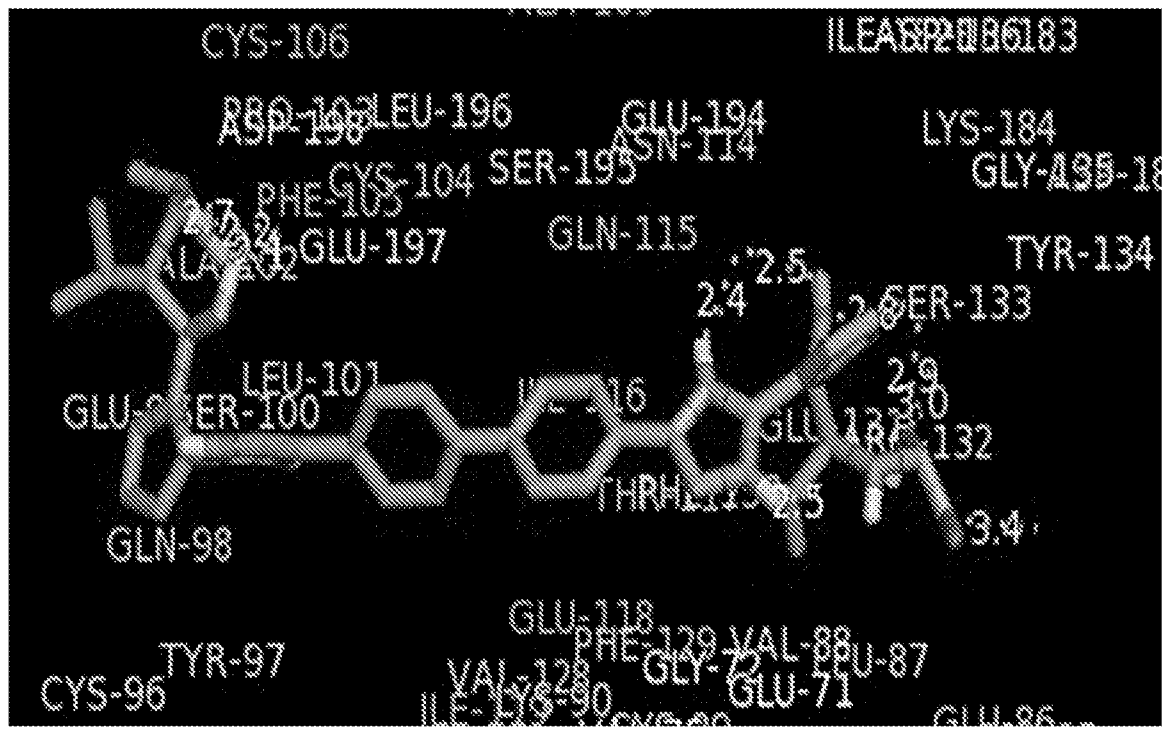
FIG. 11 shows the results of a molecular docking analysis of Trib2 (protein) and daclatasvir (ligand), presented in a view showing the ligand and spatial arrangement of amino acids of Trib2.

FIGS. 9-11 show the results of a molecular docking analysis of Trib2 (protein) and daclatasvir (ligand). Molecular docking of Daclatasvir (DCV) in the active site of TRIB2. For molecule docking, the homology model of human TRIB2 (UniProtKB ID: Q92519) was built with Swiss-Model by submitting the FASTA sequence on the server. The top-ranked model based on sequence similarity was used for the docking studies. The chemical structures of Daclatasvir (DCV) (CID 25154714) was retrieved from PubChem. The ligand (DCV) was docked to the TRIB2 model with AutoDock Vina using PyRx platform. Search space was defined as centers X=7.6566, Y=30.1191, and Z=186.2056 and the dimensions (Å) X=48.1519, Y=63.3073, and Z=40.9325. The docked complex was visualized using PyMOL molecular visualization tool. The 3-dimensional orientation of DCV in the active site binding pocket residues of the TRIB2 taking part in the hydrogen, hydrophobic, and van der Waals interactions, are highlighted.

Figure 12:
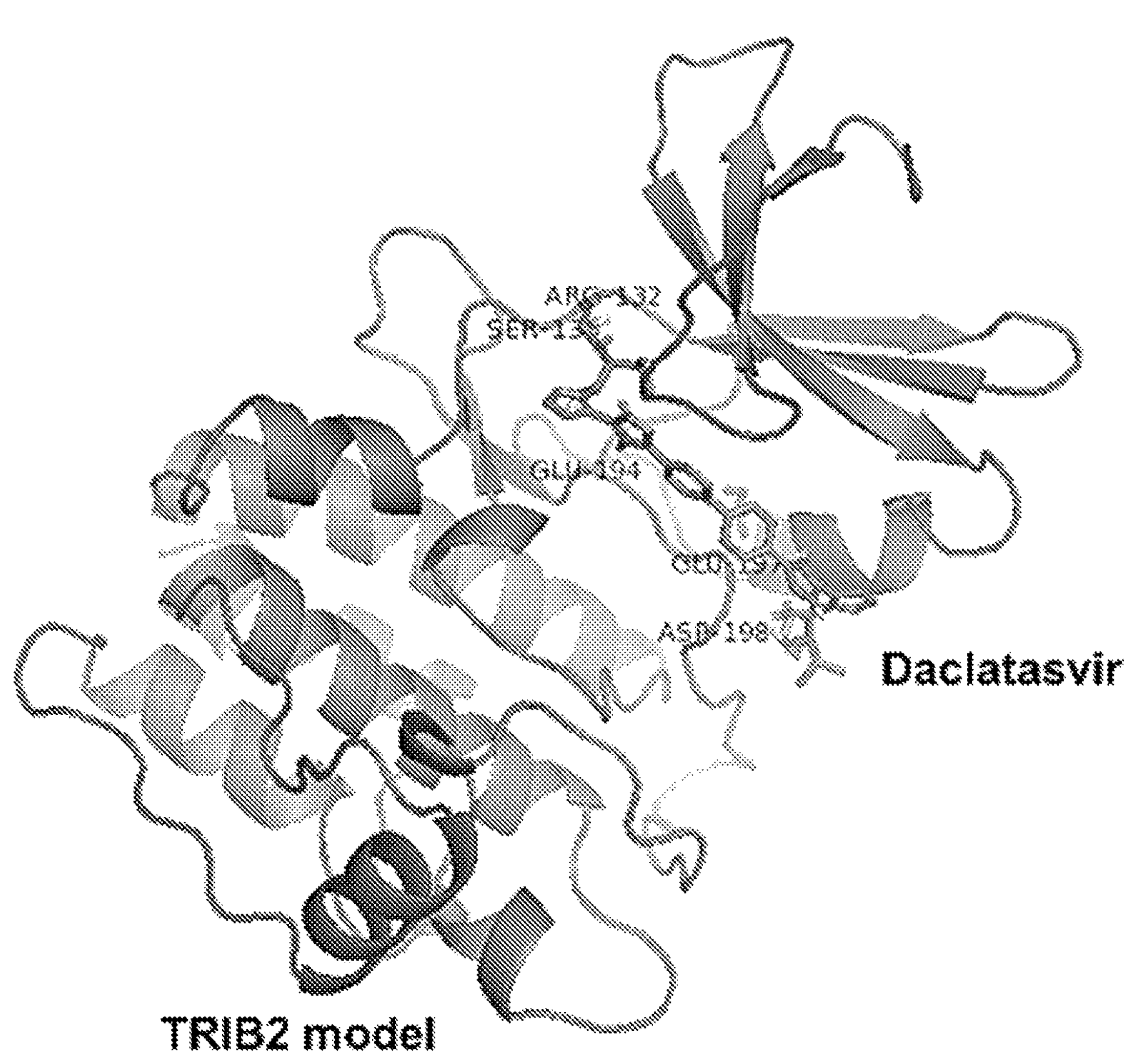
FIG. 12 depicts a 3D model showing the establishment of polar contacts between the DCV and the TRIB2. Here, Arg-132, Ser-133, Glu-194, Glu-197, and Asp-198 residues of the TRIB2 were shown to form a hydrogen bond with the DCV.

In addition, the polar contacts were established between the ligand and the protein. Arg-132, Ser-133, Glu-194, Glu-197, and Asp-198 residues of the TRIB2 were shown to form a hydrogen bond with the DCV (FIG. 12).

FIG. 13 shows the amino acid sequence of Trib2, including the residues that interact with DCV (highlighted in red).

DCV Kills ERPC Cells by Inducing Apoptosis

Figure 15:
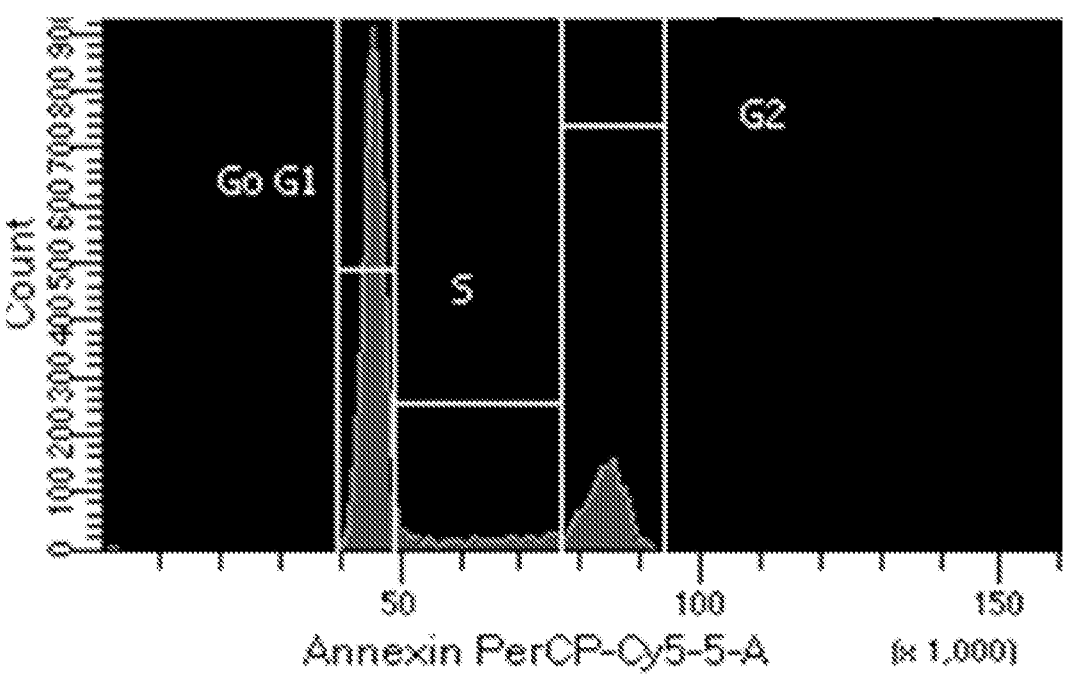
FIG. 15 depicts the flow cytometry results evaluating apoptosis in LNCaP-ENR cells treated with a Daclatasvir at varying doses for 24 hours. Cells were stained with PerCP-Cy5.5 Annexin V.
Figure 16:
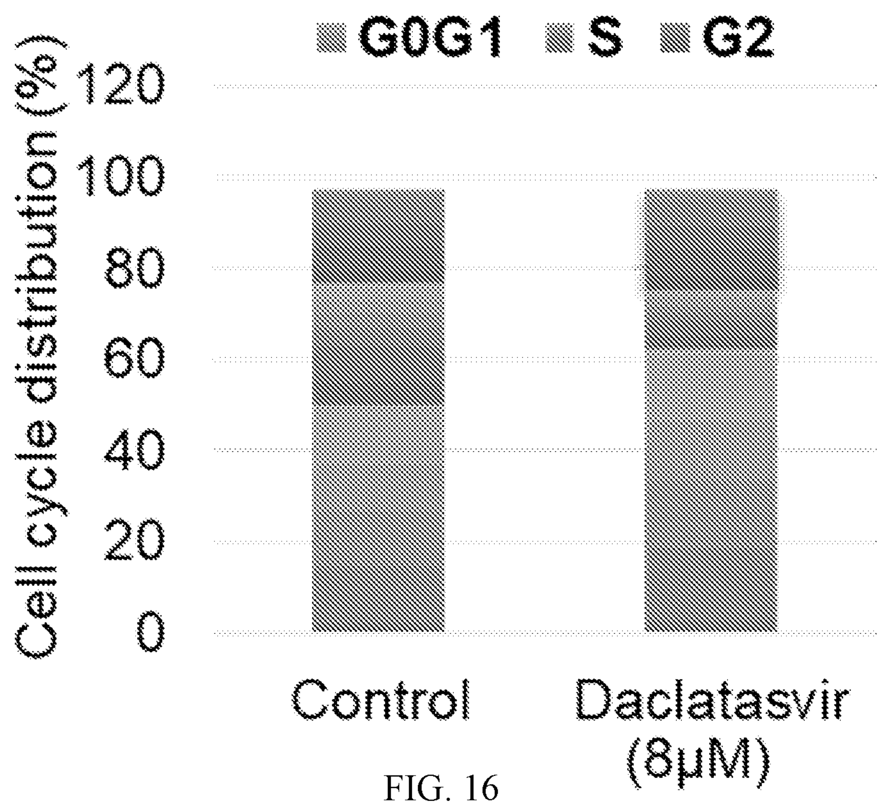
FIG. 16 shows a graph summarizing the cell cycle distribution in the control cells compared to cells treated with Daclatasvir (8 μM).

The present example illustrate that DCV effectively decreased Trib2 protein level and reduced viability of ERPC cells (FIG. 14). DCV (brand name "Daklinza") is an FDA-approved drug produced by Bristol-Myers-Squibb, and is primarily intended to be an inhibitor of HCV nonstructural protein 5A (NS5A), which is important for replication of the virus. Here, the experiments with cancer cells revealed that DCV triggers degradation of Trib2 protein and decreases the viability of ERPC cells, which opened up a new avenue for its repurposing against Trib2-overexpressing cancers, such as ERPC. Also, DCV induces apoptosis and remarkably blocked the soft-agar colony formation (an in vitro test for tumorigenicity) by ERPC cells (FIG. 15). Complete inhibition of colony formation by ERPC cells signifies that DCV can penetrate to overcome the resistance due to compactness and hypoxic environment at the core of the lumpy mass of ERPC cells. Thus, a superior in vivo effectiveness of DCV against ERPC can be expected. Also, DCV induces apoptosis and synergizes with Enzalutamide to inhibit the viability of prostate cancer cells (FIG. 16; see also FIG. 3C).

Figure 17:
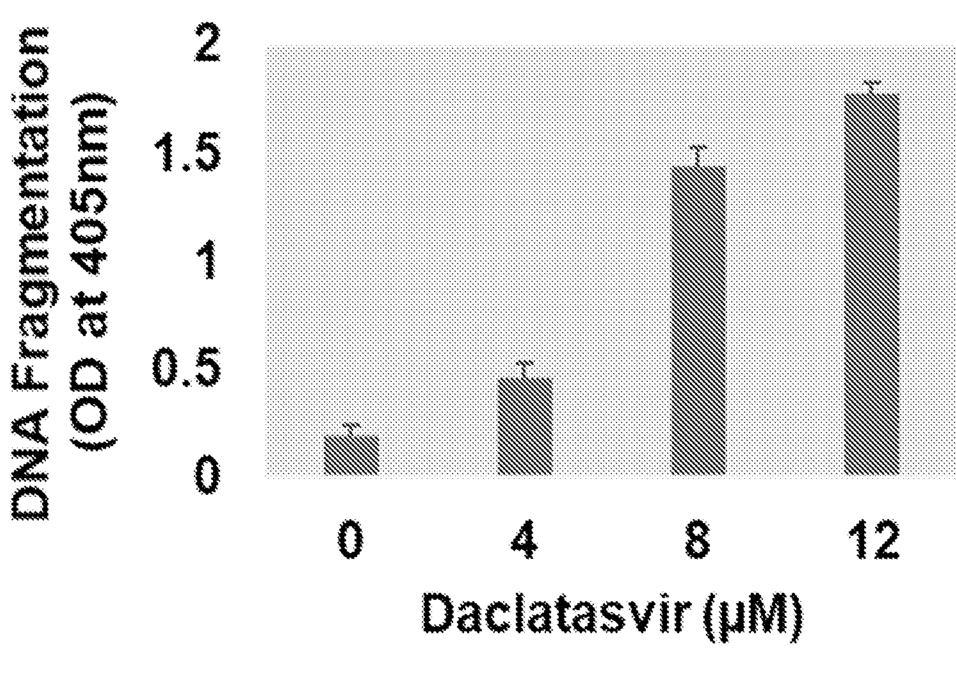
FIG. 17 depicts a graph showing the apoptotic effects of DCV as measured by DNA degradation assay.

To explore the underlying mechanism of DCV-induced apoptosis in ERPC cells, the effect of DCV on Jun N-terminal kinases (JNKs) was analyzed. JNKs play a critical role in apoptotic pathways. The present disclosure found that DCV triggers rapid and robust activation of the c-JNK in a dose-dependent manner in LNCaP-ENR cells (FIGS. 14-17). Both caspase-dependent and caspase-independent apoptotic cell death processes are known. Here, it was observed that treatment with DCV induces activation of caspase 3 in LNCaP-ENR cells (FIGS. 14-17). Moreover, it was found that the DCV treatment-induced apoptosis in ERPC is inhibited when the cells were pretreated with a caspase inhibitor, Z-VAD-FMK, suggesting that the DCV-induced apoptosis in ERPC cells is dependent on caspase activity (FIGS. 3C, 17). Interestingly, cells treated with ledipasvir (also an inhibitor of hepatitis C virus) did not show any signs of apoptotic features, suggesting that the effect of DCV to induce apoptosis in ERPC cells is highly selective.

DCV Re-Sensitizes Enzalutamide-Resistant Prostate Cancer Cells and Synergizes with Enzalutamide to Kill Prostate Cancer Cells.

The present disclosure demonstrates that DCV effectively decreased Trib2 protein level and reduced viability of ERPC cells (data not shown).

Figure 18:
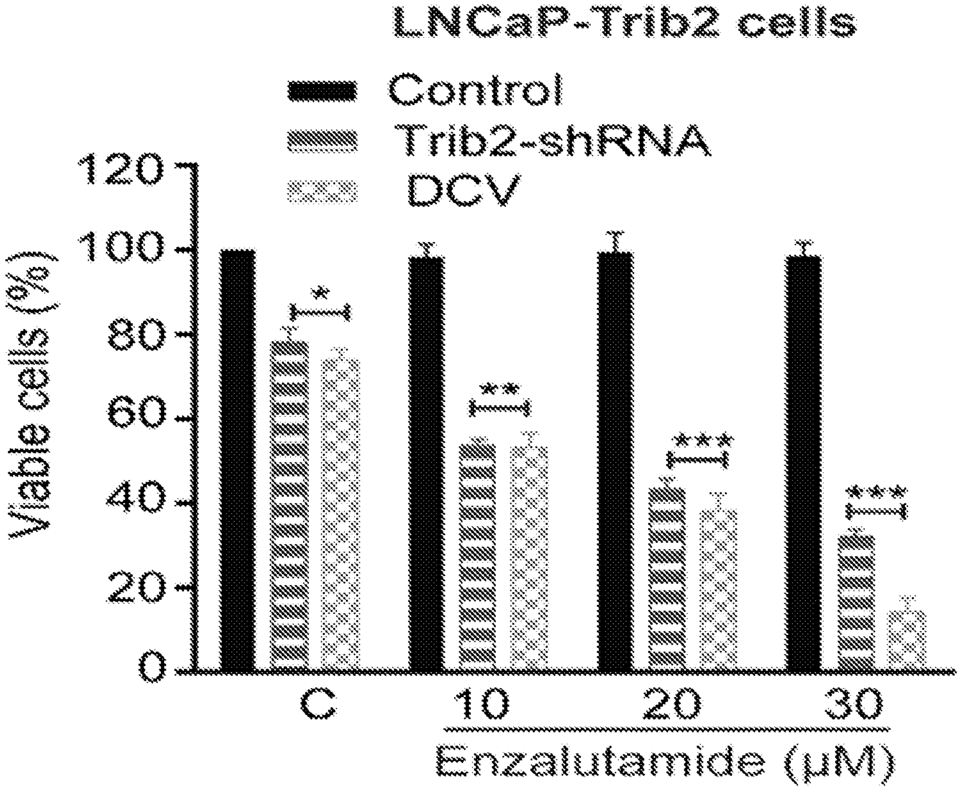
FIG. 18 depicts a graph showing the results of prostate cancer cells transfected with full length human gene to overexpress Trib2, and treated with enzalutamide. Interestingly, inhibition of Trib2 with DCV (6 μM) re-sensitizes resistant cells to enzalutamide again. Trib2 siRNA was used in parallel experiments as a positive control. Error bars show Standard Error (SE). * is $p<0.05$;  is $p<0.005$; * is $p<0.0005$.
Figure 19:
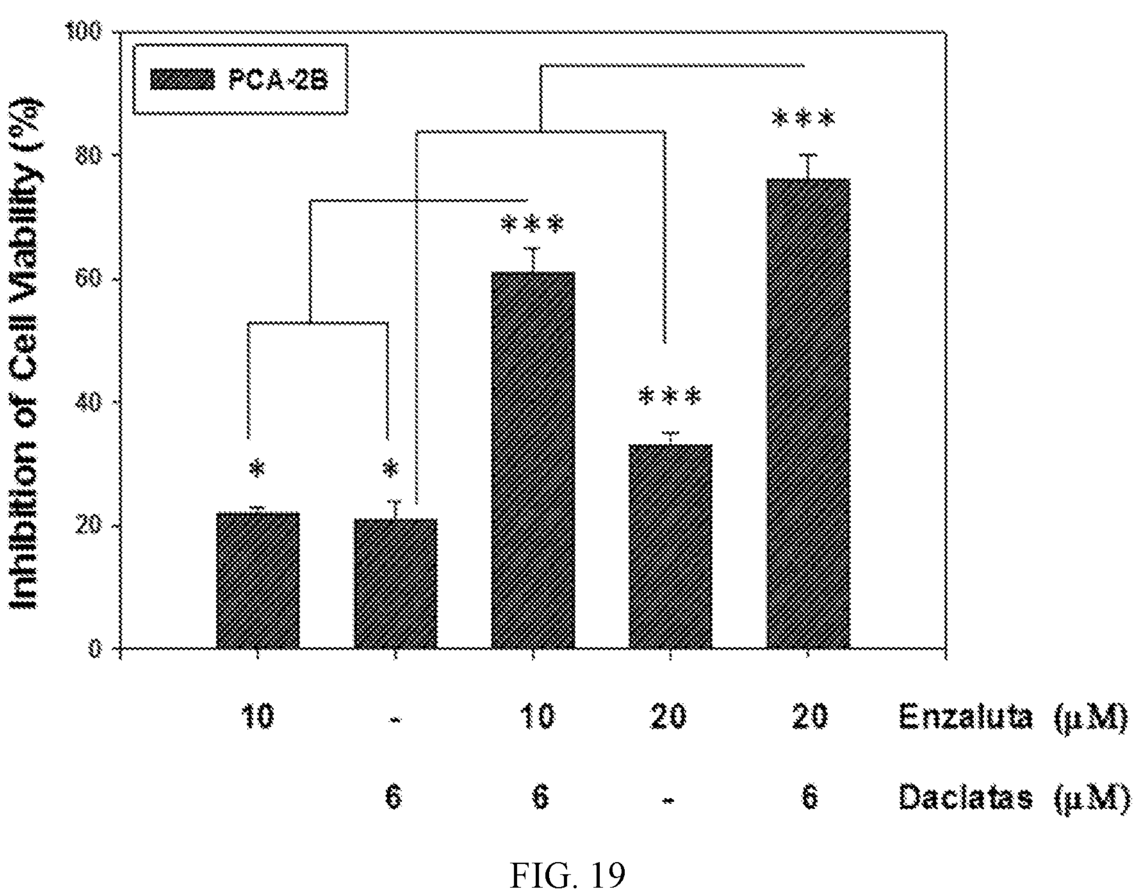
FIG. 19 depicts a graph showing the synergistic effects of DCV and Enzalutamide to inhibit cell viability of prostate cancer cells, measured by MTS/PES Assay. Error bars show Standard Error (SE). * is $p<0.05$;  is $p<0.005$; * is $p<0.0005$.

Here, FIGS. 18-19 show results demonstrating the re-sensitization of enzalutamide resistant prostate cancer cells. Prostate cancer cells were transfected with full length human gene to overexpress Trib2 (FIG. 18). Trib2-OE cells are completely resistant to clinically relevant doses of enzalutamide. Interestingly, inhibition of Trib2 with DCV (6 μM) re-sensitizes resistant cells to enzalutamide again. Trib2 siRNA was used in parallel experiments as a positive control. In addition, DCV and Enzalutamide demonstrated synergistic effects with regard to inhibition of cell viability of prostate cancer cells, as measured by MTS/PES Assay (FIGS. 3D, 19).

DCV Inhibits ERPC Tumor Growth in Nude Mice.

Figure 20:
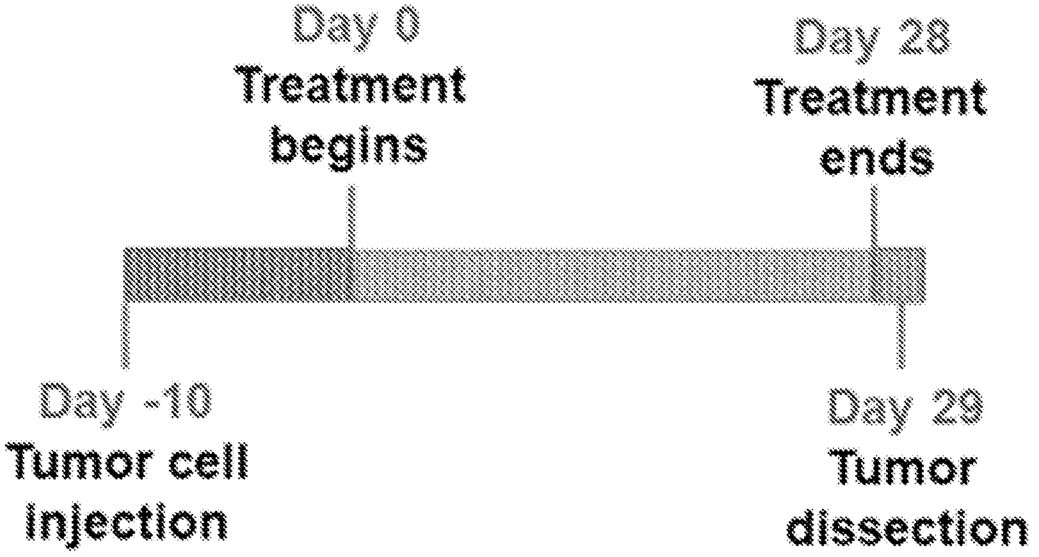
FIG. 20 shows treatment timeline for a xenograft study evaluating DCV inhibition of ERPC tumor growth in BALB/c nude mice. Briefly, BALB/c nude mice were subcutaneously injected with the highly tumorigenic-E006AA (E006AA-hT) cells ($1\times10^6$ per mouse) to develop tumors and then treated with 30 mg/kg/day DCV or solvent orally for four weeks (n=3). Tumor size and mice body weights were measured once per week.

In a pilot xenograft experiment, it was determined that DCV at 30 mg/kg/day (MTD of DCV: >200 mg/kg/day) inhibits ERPC tumor growth in nude mice without any overt toxicity to animal health (FIG. 20; see also FIGS. 4A, 4B, 4C). This is a remarkable finding which experimentally demonstrates that DCV is a suitable compound with excellent in vivo effect and provides a strong mechanistic support to the concept that the drug screening and testing of the present disclosure will be able to develop attractive Trib2-targeting agents to effectively eliminate deadly ERPC cells towards establishing a new foundation for therapy of deadly ERPC. An overview of the treatment timeline is provided in FIG. 20. Briefly, to evaluate DCV inhibition of ERPC tumor growth in BALB/c nude mice, the BALB/c nude mice were subcutaneously injected with the highly tumorigenic-E006AA (E006AA-hT) cells (1×106 per mouse) to develop tumors and then treated with 30 mg/kg/day DCV or solvent orally for four weeks (n=3). Tumor size and mice body weights were measured once per week. The results of the xenograft study are shown in FIGS. 4A-4C, and in Example 4, above.

As shown in FIG. 4C, a strong effect of DCV was observed on Trib2 and tumor growth, and no sign of overt toxicity (e.g., significant loss of animal body weight, or change in locomotion, food intake, skin color, diarrhea, color of urine, general viscera) was observed with DCV treatment for four weeks.

Discussion

Introduction of the second-generation androgen receptor blockers is one of the most remarkable achievements that happened in the last decade for prostate cancer therapy. However, in spite of its initial beneficial effect, androgen-resistant disease invariably develops which is lethal. To understand the molecular basis of the resistant phenotype the present disclosure comprehensively analyzed clinically relevant cells and tissues: this revealed that during the transition of prostate cancer from an androgen-dependent to an androgen-independent state, upregulation of the Trib2 pseudokinase is a major and critical genetic event. The present disclosure showed that Trib2 is heavily expressed in ERPC cells, and inhibition of Trib2 by shRNA downregulates Trib2 and kills ERPC cells via caspase-mediated apoptosis. The present disclosure also found that in contrast to the ERPC cells which express high levels of Trib2, the expression of Trib2 in normal, non-cancer cells (e.g., astrocytes, human fore-skin fibroblasts) is undetectable, and that the normal, non-cancer cells are not affected by Trib2 inhibition. These novel findings document a unique regulation of Trib2 oncogene and the survival of ERPC cells by Trib2-mediated signaling and suggest that targeting Trib2 may turn out to be an excellent approach to effectively and selectively eliminate the ERPC cells via induction of apoptosis, which may help establish a new foundation to overcome ERPC and prevent prostate cancer recurrence.

Though Trib2 has emerged as a new biomarker and molecular target for androgen-resistant prostate cancer, targetable agents to inhibit Trib2 activity are not commercially available. In the blinded screening performed herein, it was found that daclatasvir is a strong inhibitor of Trib2-luciferase activity showing more than 70% inhibition in 24 hours (FIG. 5, Table 3). In the counter-screen it was found that daclatasvir does not inhibit luciferase activity in the absence of Trib2, suggesting that daclatasvir interacts with Trib2, rather than the luciferase itself.

Interestingly, while daclatasvir inhibits Trib2-luciferase activity, several other anti-viral compounds, such as ledipasvir, dolutegravir, darunavir, and penciclovir were not effective, which suggests that a critical structural component of the daclatasvir molecule is needed to inhibit Trib2. Daclatasvir is a direct-acting antiviral agent (DAA) against the hepatitis C virus. Thus, the design of a luciferase-tagged fusion protein-based assay and thermal shift assay, of the present disclosure, to screen a library of compounds to find daclatasvir as an inhibitor of Trib2 via direct binding is a ground-breaking observation.

The results have shown for the first time that the anti-viral compound, DCV, inhibits Trib2 and kills ERPC cells. Trib2 is believed to be a very promising molecular target for development of new therapies against ERPC which is currently incurable. Lack of an effective chemical inhibitor to inhibit Trib2 and kill the ERPC cells is primarily delaying development of an effective therapy for ERPC. Daclatasvir (trade name Daklinza) is an FDA-approved an anti-hepatitis C viral drug. Based on the ALLY-3 randomized, multicenter, open-label, active-controlled clinical trial using 60 mg daclatasvir (equivalent to 66 mg daclatasvir dihydrochloride) along with 400 mg of sofosbuvir (Sovaldi) via once daily oral dose for 12 weeks in 152 patients (NCT02319031), daclatasvir was given approval for use in hepatitis c virus (HCV) infection in July of 2015. Daclatasvir was primarily intended to be an inhibitor of HCV non-structural protein 5A (NS5A), which is an important component of the viral RNA replication complex. NS5A is a zinc binding, proline-rich phosphoprotein and plays a crucial role in the replication of HCV. Daclatasvir is freely soluble in aqueous solvents and its uptake rate is about 67% when delivered orally. It is very well tolerated in mammalian hosts with a half-life of about 15 hours and stays mostly as protein bound (~99%) in vivo. Metabolism of daclatasvir (a biphenyl-carbamate) is mainly through liver and it is an inhibitor of p-glycoprotein (PGP). Thus, daclatasvir possesses excellent pharmacological properties though direct effect of daclatasvir on mammalian cells is not well studied, and its effect on cancer cells has never been tested before.

In a cell culture system, it was determined that DCV substantially decreased the protein level of Trib2 within 24 hours. Presumably this happened due to direct interaction of the Trib2 protein with DCV which changed its ubiquitination status, followed by degradation via proteasome activation. Enhanced degradation of Trib2 protein corresponds to the decrease of its downstream targets, such as p-Akt, Bcl-xL and surviving (FIGS. 2A, 2B, 3A, 3B, 6 and 7). Also, as expected, DCV treatment increased the protein level of the tumor suppressor, FOXO3-alpha, presumably via inhibition of Trib2 which is otherwise downregulated by Trib2 via activation of Akt.

Therapy-resistant cancer cells develop extraordinary ability to invade surrounding tissues, move to distant sites and recolonize to generate metastatic nodules which ends up with. Here, it was found that DCV strongly inhibits in vitro matrigel invasion (data not shown) and soft-agar colony formation (FIG. 3B), by both LNCaP-ENR and PCA-2B-ENR cells at sub-lethal doses. The in vitro findings of a dramatic reduction of invasive as well soft-agar colony forming abilities of ERPC cells by DCV suggests that the aggressive and metastatic tumor-forming ability of ERPC cells could be effectively controlled by DCV or similar other agents. The present disclosure also observed that treatment with DCV decreases the viability of Enzalutamide-resistant prostate cancer cells. DCV severely alters the morphology (data not shown), and decreases the viability (FIGS. 3D, 18, and 18), of enzalutamide-resistant LNCaP-ENR and PCA-2B-ENR prostate cancer cells in a clear dose-dependent manner. Similarly, morphological alterations and a decrease in viability was also found when the ERPC cells were treated with Trib2 shRNA, confirming a critical role of Trib2 in the viability of ERPC cells (FIG. 3B). The present disclosure provides an effective, novel, therapeutic strategy against aggressive, enzalutamide-resistant, lethal prostate cancer.

The thermal shift assay showed that DCV directly interacted with the Trib2 protein and destabilized it which is reflected by the temperature needed to denature the pure protein when compared with DMSO only ($T_m$ decreased from 41° C. to 37° C. (FIG. 8). The 3-dimensional orientation of DCV in the active site of the TRIB2 (FIG. 9) The polar contacts established between the ligand and the protein. Arg-132, Ser-133, Glu-194, Glu-197, and Asp-198 residues of the TRIB2 formed a hydrogen bond with the DCV (FIG. 10). The binding pocket residues of the TRIB2 taking part in the hydrogen, hydrophobic, and van der Waals interactions, are highlighted. The present disclosure found that DCV vertically checks the cell cycle progression by arresting them at G0/G1 phase (FIGS. 14-16). DCV-induced morphological changes in prostate cancer cells reminded us about induction of apoptosis. Thus, the mechanism of cell death was characterized, and found enhanced annexin V binding which corresponds to externalization of phosphatidylserine within hours of DCV treatment (FIGS. 15 and 16). Moreover, it was observed that DCV triggers degradation of chromatin DNA to nucleosomal fragments, suggesting that ERPC cells are undergoing apoptosis with DCV treatment (FIG. 17). ERPC cells are characterized by rapid growth and metastasis which deteriorates health of prostate cancer patients towards a lethal phenotype. Thus, the induction of apoptotic death in ERPC cells is a significant event which may be useful to debulk tumor load by killing cancer cells.

Anti-androgenic therapies are commonly used in the clinic which extends lifespan, but castration-resistant disease invariably develops. More than 90% of the CRPC patients end up with bone metastasis causing excruciating pain and suffering. While Enzalutamide, an FDA-approved inhibitor of androgen receptor, improves survival and quality of life in CRPC patients, which highlights the success of targeting the AR axis in CRPC, these therapies are not curative because development of resistant disease is inevitable, and because the resistant cells are not killed effectively by available other clinical regimens. The present disclosure revealed that DCV re-sensitizes ERPC cells to enzalutamide, which suggests that DCV removes a major obstacle in the resistance mechanism (FIGS. 18 and 19). This finding may have enormous impact in developing a new therapy for ERPC. And, The present disclosure also found that DCV is effective in vivo to reduce ERPC tumor growth (FIGS. 4A-4C and 20). ERPC in interesting because enzalutamide, which is prescribed post-docetaxel failure, extends lifespan but no effective treatment option remains when enzalutamide-resistance develops. Nonetheless to say that currently most of the men's lives lost due to prostate cancer is because of the development of ERPC. Thus, the findings of the present disclosure provide additional support to further examine DCV towards clinical development, because DCV is already approved by the FDA and is a well-tolerated drug for human use.

Example 6. Activity of DCV Against Lung Cancers

Tribbles 2 is overexpressed in a range of cancer types, such as melanoma, lung, prostate, myeloma, kidney, ovarian, pancreatic cancer. Thus, daclatasvir (DCV) was tested on a range of cancer cells where Tribbles 2 is overexpressed (lung, kidney, pancreas). Based on the data presented herein, and without wishing to be bound by theory, DCV may serve as a good drug for therapy of several other types of cancer, in addition to prostate cancer.

Figure 21:
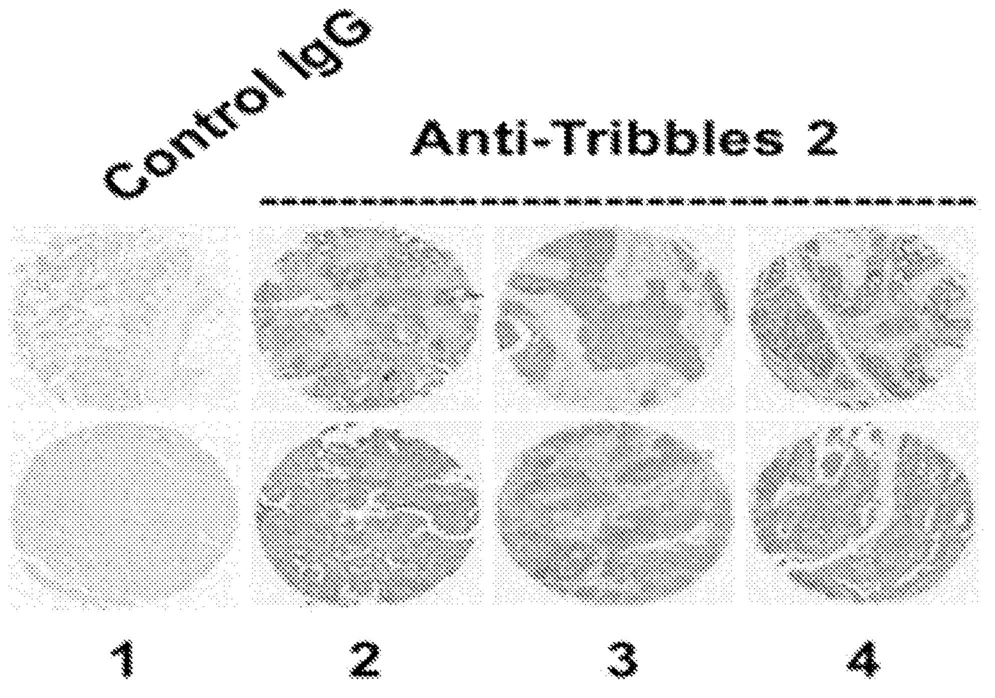
FIG. 21 shows the immunohistochemistry of tumor sections stained with anti-Trib2 antibody. Tumor type is as follows: (1) human patient lung adenocarcinoma; (2) human patient lung papillary carcinoma; (3) human patient lung squamous cell carcinoma; and (4) human patient lung adenocarcinoma.
Figure 22:
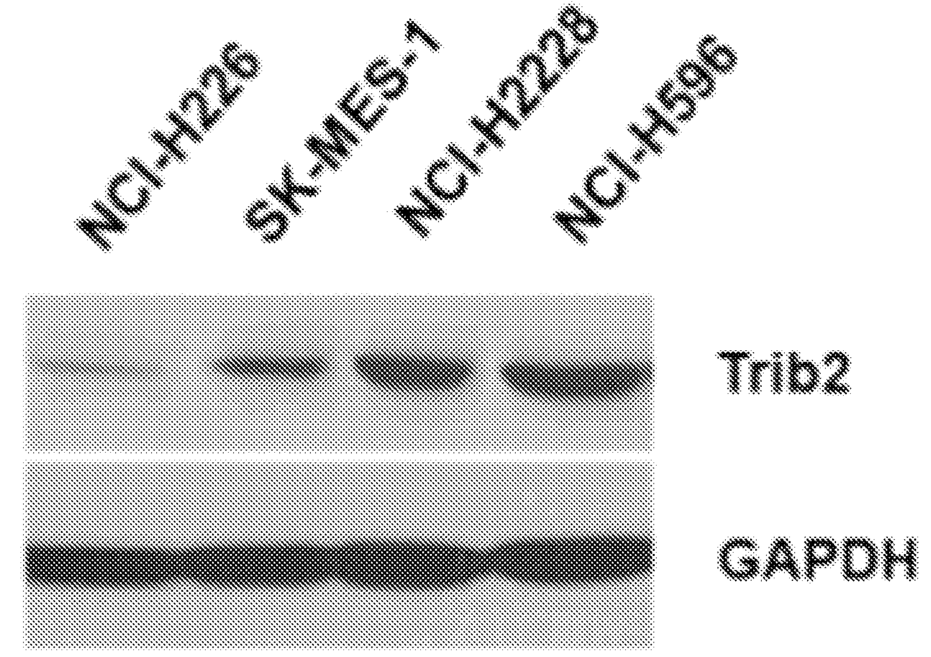
FIG. 22 shows a Western blot evaluating Trib2 protein level in lung cancer cell lines. Each lane corresponds to the following cell line: NCI-H226 and SK-MES-1=Squamous cell carcinoma; NCI-H2228=Non-small cell lung cancer; and NCI-H596=Adenocarcinoma.
Figure 23:
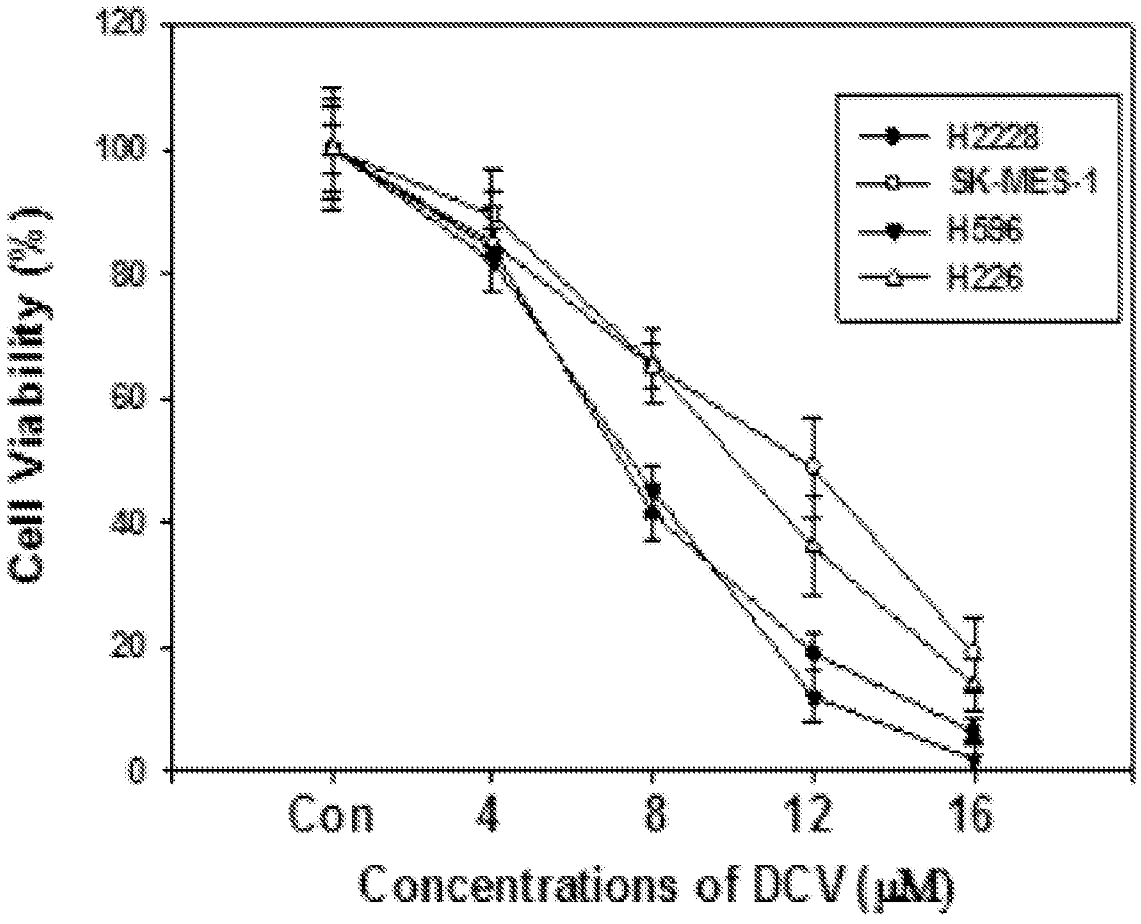
FIG. 23 shows the results of a 72-hour cell viability assay in lung cancer cell lines, treated with DCV. The lung cancer cell lines are as follows: NCI-H226 and SK-MES-1=Squamous cell carcinoma; NCI-H2228=Non-small cell lung cancer; and NCI-H596=Adenocarcinoma. Error bars show Standard Error (SE).

Lung cancer studies were performed as follows: Trib2 was detected by immunohistochemistry (IHC) using anti-Trib2 antibody at 1:100 (Cell Signaling Tech) in tumor sections. The tumors evaluated were: (1) Adenocarcinoma; (2) Papillary carcinoma; (3) Squamous cell carcinoma; and (4) Adenocarcinoma; and all tumors were human patient lung tumor samples. (FIG. 21). In addition, Trib2 protein level in cell lines in cell culture lines obtained from ATCC. was detected by Western blot (FIG. 22). As shown in FIG. 23, DCV effectively kills a range of lung cancer cells in a 72-hour cell viability assay, e.g., the following lung cancer cell lines: NCI-H226 and SK-MES-1=Squamous cell carcinoma; NCI-H2228=Non-small cell lung cancer; and NCI-H596=Adenocarcinoma.

Example 7. Methods of Treatment of Prostate Cancer and Metastatic Prostate Cancer The present disclosure provides a prophetic example of a phase I dose escalation trial of daclatasvir (DCV) in patients with metastatic, enzalutamide-resistant prostate cancer (ERPC). The primary objective of the trial is to determine a recommended phase II dose for daclatasvir in prostate cancer. Here, both the safety and pharmacokinetic (PK) data may be taken into consideration when determining the RP2D. The RP2D may be established if steady state PK data reaches a concentration of 4 μM, an effective concentration in the pre-clinical prostate cancer modeling (see, e.g., FIGS. 2B, 3A, 3B, 4B, and 4C). Dose-escalation may continue until the goal plasma concentration is reached, or until a maximum-tolerated dose is obtained.

Dose escalation may start with daclatasvir 60 mg orally daily, which is the current FDA-approved dose for patients with hepatitis C. The doses tested may be 60 mg orally daily; 60 mg orally twice daily; 60 mg by mouth ("po") three times daily; and if necessary, a maximum of 120 mg twice daily. Because median peak plasma concentration after one dose of 60 mg DCV is ~2 μg/ml (2.5 μM), a 2-fold escalation may be all that is necessary to achieve the target plasma concentration of 4 μM. DCV has previously been reported to be well tolerated at a dose of 100 mg po daily. DCV may be administered in 28-day cycles.

Figure 24:
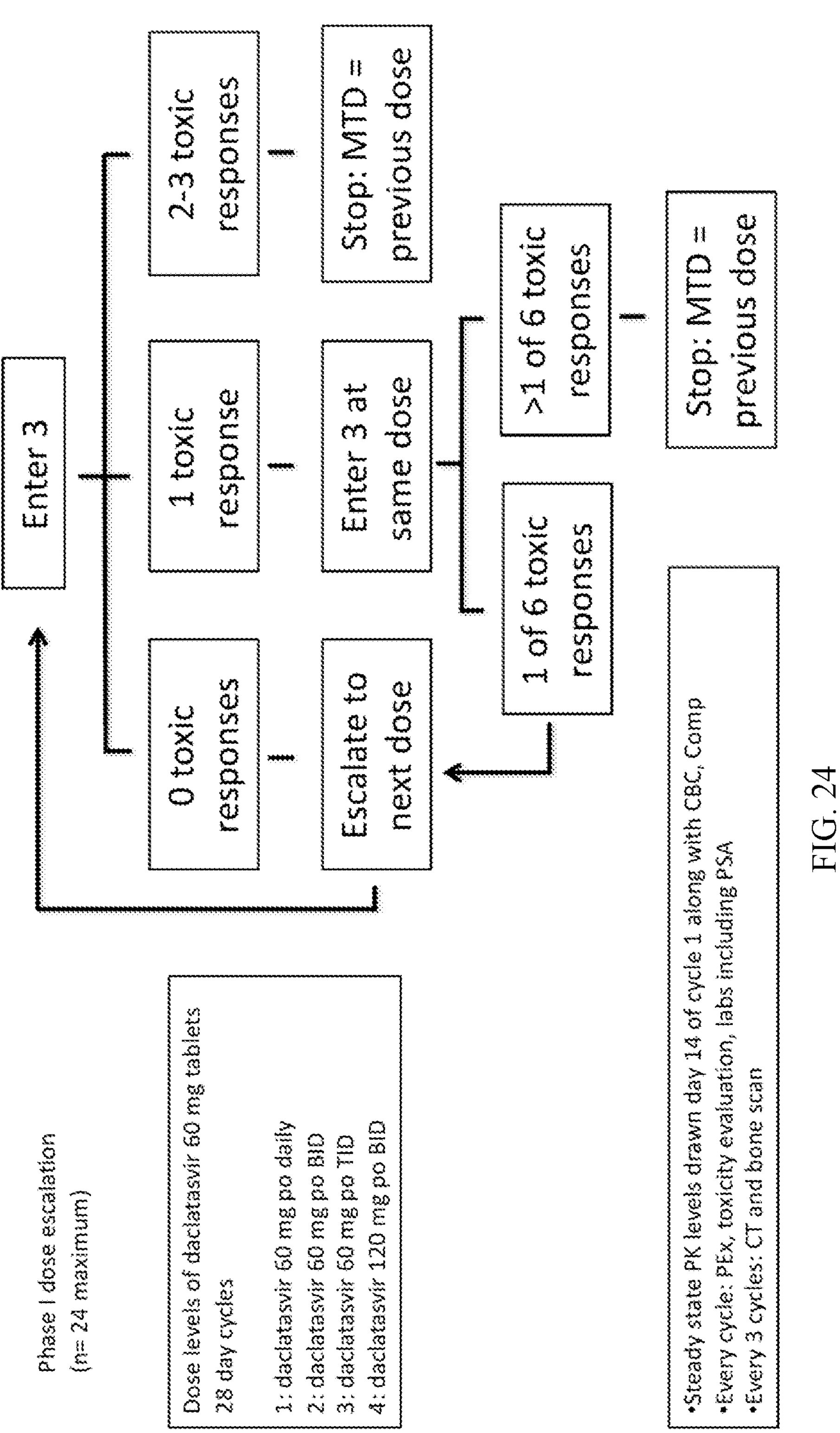
FIG. 24 shows a dose escalation design schematic for a phase I dose escalation trial of daclatasvir (DCV) in patients with metastatic, enzalutamide-resistant prostate cancer (ERPC). "MTD"=maximum-tolerated dose; "PK"=pharmacokinetic.

A modified 3+3 dose escalation design may be implemented (FIG. 24). Successive cohorts of participants (3 participants/cohort) may be each started on a fixed dose of DCV. Dose escalation may be continued until dose limiting toxicities (DLTs) are observed in >33% of participants or the prespecified plasma concentration is reached. If no DLTs are observed at a certain dose level, a new cohort may be enrolled at the next planned dose level. If DLTs are observed in 1 participant in the cohort, another 3 participants may be treated with the same dose level. The maximum-tolerated dose (MTD) is defined as 1 dose level below the dose in which DLTs are observed in >33% of the participants. That is, if DLTs are observed in at least 2 of 3 participants, the MTD is determined to be the dose administered to the previous cohort. Similarly, in a cohort of 6 participants, 3 of 6 participants may have to experience DLTs to determine the MTD. If at any dose level, the plasma concentration is satisfied, dose escalation will be stopped. The optimal phase II dose is the dose level where prespecified plasma concentrations are achieved without surpassing the MTD.

Peak plasma concentrations of DCV are reached between 1-2 hours after dosing and the mean terminal half-life of DCV is 12-15 hours. Steady state levels are reached after three days of administration. Therefore, PK samples may be drawn 1.5 hours after DCV administration on C1D14 to assess steady state peak DCV plasma concentrations. Plasma DCV concentrations may be determined using a Waters Acquity UPLC BEH C18 reversed phase (2.1×100 mm, 1.7 μm) column. Elution of the samples may be achieved using a mobile phase composed of 9 mM dipotassium hydrogen orthophosphate buffer (pH 4±0.1 adjusted with o-phosphoric acid):acetonitrile (60:40 v/v). The prepared mobile phase may be filtered with 0.45 μm membrane filter and degassed for 30 min in an ultrasonic bath before being used. Flow rate may be 0.1 mL/min and the injection volume may be 10 μL. Column temperature may be maintained at 40° C. Equilibrium, conditioning, and pre-washing of the stationary phase may be done for 30-45 min.

Adverse events may be monitored throughout the study. Patients may come for history, physical, and bloodwork on day 1 of each cycle. Bloodwork may be used to assess hematologic, kidney and liver function. Toxicity may be graded with Common Terminology Criteria for Adverse Events v5.0. An independent medical monitor will be appointed to review study data make recommendations on stopping the trial if excess toxicity is observed. CT and bone scan may be performed every 3 cycles.

Preliminary efficacy evidence of DCV may be derived based on the PSA response rate (at least 50% PSA decline), disease control rate (DCR) and overall survival (OS) at 6 months. Previous data suggests that Trib2 is overexpressed in in enzalutamide-resistant prostate cancer. In an exploratory analysis, the PSA response rate may be described separately in positive and negative Trib2 expression patients evaluated using pre-treatment biopsy samples. Statistical hypothesis testing is optional.

Study Population: The protocol may enroll men with histologically confirmed, metastatic prostate cancer that has progressed after enzalutamide treatment. Prior enzalutamide treatment and prior docetaxel therapy are required. Patients should have exhausted or refused further standard-of-care therapies. DCV carries warnings for hepatitis B reactivation, bradycardia and hypoglycemia, so these conditions will be exclusionary.

Daclatasvir is a substrate of CYP3A and carries the potential for drug-drug interactions. Additional eligibility criteria may include:

Age>18 years old, KPS>70%

No investigational agents received in prior 14 days

No active brain metastases, psychiatric illness, TIA or CVA in the past 6 months, active infection (including HIV), active secondary malignancy or other significant uncontrolled intercurrent illness.

Any patient with uncontrolled diabetes or an episode of hypoglycemia in the past month is ineligible Patients with cardiac disease will be ineligible if they have Class III or IV CHF, unstable angina, require amiodarone therapy, or have a history of heart block or bradyarrhythmia Patients who require treatment with strong CYP3A4 inducers and inhibitors are ineligible.

No evidence of current or prior HBV or HCV infection

Adequate organ function is required as evidenced by ANC>100K, Platelets>100K, Total Bilirubin<1.5×ULN, AST/ALT<3.0×ULN, CrCl>50 ml/min, Hemoglobin>9 gm/dL, Serum Albumin>2.8 gm/dL Sample Size Justification: Based on the methodology described above, the minimum sample size required to determine the RP2D is three patients. There is no DLT anticipated at the starting dose, and if the target plasma concentration is achieved in the three patients treated at this level, 60 mg po daily may be the RP2D. If the target plasma concentration is not met at any of the lower dose levels, and if DLT requires cohort expansion at every dose level, the maximum sample size required will be six patients treated at each of the four dose levels, or 24 total patients.

Feasibility: The historical accrual for metastatic castration-resistant prostate cancer (mCRPC) clinical trials at, e.g., a site such as Henry Ford Hospital, Henry Ford Health System, Detroit campus (2799 E Grand Blvd, Detroit, MI 48202) is approximately one to two per month. Patients may be actively recruited from additional hospital, regional health centers, and/or satellites (e.g., satellites and regional centers within the Henry Ford Cancer Institute (HFCI), such as Allegiance, Macomb, Wyandotte), providing an opportunity to approximately double the eligible patient population. Because the target patient population for this phase I trial is mCRPC patients who have exhausted standard options, an increased pool of patients willing to participate across all HFCI sites is anticipated. And, with a total accrual of approximately two to three patients per month, completing the accrual in less than 12 months is likely feasible.

The invention claimed is:

1. A method of treating cancer in a subject in need thereof, said method comprising administering to the subject a therapeutically effective amount of daclatasvir (DCV), wherein cancer cells in the subject express higher levels of Tribbles homolog 2 (TRIB2) compared to levels of TRIB2 expressed by counterpart non-cancer cells, wherein: (i) the counterpart non-cancer cells are derived from the subject; and/or (ii) the counterpart non-cancer cells are derived from a subject not suffering from cancer, and wherein the cancer cells and the counterpart non-cancer cells are derived from prostate tissue; wherein, optionally, the cancer cells and the counterpart non-cancer cells are cells of prostate glands.

2. A method of treating cancer in a subject in need thereof, said method comprising administering to the subject a therapeutically effective amount of daclatasvir (DCV), wherein cancer cells in the subject express higher levels of Tribbles homolog 2 (TRIB2) compared to levels of TRIB2 expressed by counterpart non-cancer cells, wherein: (i) the counterpart non-cancer cells are derived from the subject; and/or (ii) the counterpart non-cancer cells are derived from a subject not suffering from cancer, and wherein the cancer cells and the counterpart non-cancer cells are derived from lung tissue; wherein, the cancer cells are, or derived from non-small cell lung cancer (NSCLC), small cell lung cancer, adenocarcinomas, squamous cell carcinomas, bronchioalveolar carcinomas, and large cell carcinomas.

* * * * *

SEQUENCE LISTING

```
<160> NUMBER OF SEQ ID NOS: 1

<210> SEQ ID NO 1
<211> LENGTH: 343
<212> TYPE: PRT
<213> ORGANISM: Homo sapiens

<400> SEQUENCE: 1

Met Asn Ile His Arg Ser Thr Pro Ile Thr Ile Ala Arg Tyr Gly Arg
1               5                   10                  15

Ser Arg Asn Lys Thr Gln Asp Phe Glu Glu Leu Ser Ser Ile Arg Ser
            20                  25                  30

Ala Glu Pro Ser Gln Ser Phe Ser Pro Asn Leu Gly Ser Pro Ser Pro
        35                  40                  45

Pro Glu Thr Pro Asn Leu Ser His Cys Val Ser Cys Ile Gly Lys Tyr
    50                  55                  60
```

-continued

```
Leu Leu Leu Glu Pro Leu Glu Gly Asp His Val Phe Arg Ala Val His
65                  70                  75                  80

Leu His Ser Gly Glu Glu Leu Val Cys Lys Val Phe Asp Ile Ser Cys
                85                  90                  95

Tyr Gln Glu Ser Leu Ala Pro Cys Phe Cys Leu Ser Ala His Ser Asn
            100                 105                 110

Ile Asn Gln Ile Thr Glu Ile Ile Leu Gly Glu Thr Lys Ala Tyr Val
        115                 120                 125

Phe Phe Glu Arg Ser Tyr Gly Asp Met His Ser Phe Val Arg Thr Cys
    130                 135                 140

Lys Lys Leu Arg Glu Glu Glu Ala Ala Arg Leu Phe Tyr Gln Ile Ala
145                 150                 155                 160

Ser Ala Val Ala His Cys His Asp Gly Gly Leu Val Leu Arg Asp Leu
                165                 170                 175

Lys Leu Arg Lys Phe Ile Phe Lys Asp Glu Glu Arg Thr Arg Val Lys
            180                 185                 190

Leu Glu Ser Leu Glu Asp Ala Tyr Ile Leu Arg Gly Asp Asp Asp Ser
        195                 200                 205

Leu Ser Asp Lys His Gly Cys Pro Ala Tyr Val Ser Pro Glu Ile Leu
    210                 215                 220

Asn Thr Ser Gly Ser Tyr Ser Gly Lys Ala Ala Asp Val Trp Ser Leu
225                 230                 235                 240

Gly Val Met Leu Tyr Thr Met Leu Val Gly Arg Tyr Pro Phe His Asp
                245                 250                 255

Ile Glu Pro Ser Ser Leu Phe Ser Lys Ile Arg Arg Gly Gln Phe Asn
            260                 265                 270

Ile Pro Glu Thr Leu Ser Pro Lys Ala Lys Cys Leu Ile Arg Ser Ile
        275                 280                 285

Leu Arg Arg Glu Pro Ser Glu Arg Leu Thr Ser Gln Glu Ile Leu Asp
    290                 295                 300

His Pro Trp Phe Ser Thr Asp Phe Ser Val Ser Asn Ser Ala Tyr Gly
305                 310                 315                 320

Ala Lys Glu Val Ser Asp Gln Leu Val Pro Asp Val Asn Met Glu Glu
                325                 330                 335

Asn Leu Asp Pro Phe Phe Asn
            340
```